United States Patent
Frank et al.

(10) Patent No.: US 11,131,737 B2
(45) Date of Patent: Sep. 28, 2021

(54) JOINT ESTIMATION DIFFUSION IMAGING (JEDI)

(71) Applicant: THE REGENTS OF THE UNIVERSITY OF CALIFORNIA, Oakland, CA (US)

(72) Inventors: Lawrence R. Frank, San Diego, CA (US); Vitaly L. Galinsky, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/893,344

(22) Filed: Jun. 4, 2020

(65) Prior Publication Data
US 2020/0386839 A1   Dec. 10, 2020

Related U.S. Application Data

(60) Provisional application No. 62/857,185, filed on Jun. 4, 2019.

(51) Int. Cl.
*G01R 33/563* (2006.01)
*A61B 5/055* (2006.01)
*G01R 33/56* (2006.01)

(52) U.S. Cl.
CPC ........ *G01R 33/56341* (2013.01); *A61B 5/055* (2013.01); *G01R 33/5608* (2013.01)

(58) Field of Classification Search
CPC .............................. G01R 33/546; A61B 5/055
See application file for complete search history.

(56) References Cited

U.S. PATENT DOCUMENTS

| | | |
|---|---|---|
| 6,611,615 B1 | 8/2003 | Christensen |
| 6,992,484 B2 | 1/2006 | Frank |
| 7,106,891 B2 | 9/2006 | Wyman et al. |
| 7,639,896 B2 | 12/2009 | Sun et al. |
| 7,672,790 B2 | 3/2010 | McGraw et al. |
| 7,773,074 B2 | 8/2010 | Arenson et al. |
| 8,742,754 B2 | 6/2014 | Hasan |

(Continued)

FOREIGN PATENT DOCUMENTS

WO    2014144331 A1    9/2014

OTHER PUBLICATIONS

Ashburner, John; "A fast diffeomorphic image registration algorithm", NeuroImage, 2007, vol. 38, pp. 95-113.

(Continued)

*Primary Examiner* — Gregory H Curran
(74) *Attorney, Agent, or Firm* — Eleanor Musick; Musick Davison LLP

(57) ABSTRACT

A method and for estimating local diffusion anisotropy and global tractography within neural architecture from diffusion weighted magnetic resonance image (dMRI) data uses a computer processor to integrate a first dataset comprising standard single pulsed field gradient (sPFG) dMRI data with a second dataset comprising double pulsed field gradient (dPFG) dMRI data into a common coordinate system with the same spatial resolution. The resulting image includes integrated macroscopic and microscopic anisotropy and global tractography within the target volume.

15 Claims, 14 Drawing Sheets
(10 of 14 Drawing Sheet(s) Filed in Color)

(56) References Cited

U.S. PATENT DOCUMENTS

| | | |
|---|---|---|
| 9,204,835 B2 | 12/2015 | Parsey et al. |
| 9,404,986 B2 | 8/2016 | White et al. |
| 9,453,940 B2 | 9/2016 | Sasaki |
| 9,645,212 B2 | 5/2017 | Frank et al. |
| 9,754,371 B2 | 9/2017 | Kateb et al. |
| 10,297,022 B2 | 5/2019 | Frank et al. |
| 10,789,713 B2 | 9/2020 | Frank et al. |
| 10,909,414 B2 | 2/2021 | Frank et al. |
| 2005/0054910 A1 | 3/2005 | Tremblay et al. |
| 2005/0119834 A1 | 6/2005 | Kita et al. |
| 2005/0154701 A1 | 7/2005 | Parunak et al. |
| 2005/0213809 A1 | 9/2005 | Lees et al. |
| 2006/0259282 A1 | 11/2006 | Failla et al. |
| 2007/0036402 A1 | 2/2007 | Cahill et al. |
| 2007/0049817 A1 | 3/2007 | Preiss et al. |
| 2007/0087756 A1 | 4/2007 | Hoffberg |
| 2008/0091388 A1 | 4/2008 | Failla et al. |
| 2008/0287796 A1 | 11/2008 | Kiraly et al. |
| 2009/0010540 A1 | 1/2009 | Mullick et al. |
| 2009/0080604 A1 | 3/2009 | Shores et al. |
| 2009/0161933 A1 | 6/2009 | Chen |
| 2010/0172567 A1 | 7/2010 | Prokoski |
| 2011/0201935 A1 | 8/2011 | Collet-Billon et al. |
| 2011/0255763 A1 | 10/2011 | Bogoni et al. |
| 2011/0297369 A1 | 12/2011 | Kumaran et al. |
| 2013/0259340 A1 | 10/2013 | Tseng et al. |
| 2013/0342206 A1 | 12/2013 | Ugurbil |
| 2014/0153797 A1 | 6/2014 | Wan et al. |
| 2014/0192046 A1 | 7/2014 | Paragios et al. |
| 2014/0249787 A1 | 9/2014 | López et al. |
| 2015/0228073 A1* | 8/2015 | Jensen ............ G01R 33/56341 382/131 |
| 2016/0004972 A1 | 1/2016 | Alboszta et al. |
| 2016/0110911 A1 | 4/2016 | Frank et al. |
| 2016/0180526 A1 | 6/2016 | Satoh et al. |
| 2016/0210742 A1 | 7/2016 | Weiss et al. |
| 2016/0225146 A1 | 8/2016 | Frank et al. |
| 2016/0343127 A1 | 11/2016 | Miller et al. |
| 2016/0343129 A1 | 11/2016 | Novikov et al. |
| 2016/0356873 A1* | 12/2016 | Topgaard ............... A61B 5/055 |
| 2017/0103533 A1 | 4/2017 | Brokman et al. |
| 2017/0220900 A1* | 8/2017 | Boada ................. G06K 9/6247 |
| 2017/0337824 A1 | 11/2017 | Chen |

OTHER PUBLICATIONS

Assemial et al., "Recent advances in diffusion MRI modeling: Angular and radial reconstruction", Elsevier, Medical Image Analysis, 15 (2011) 369-396.

Balmforth et al., Pattern formation in hamiltonian systems with continuous spectra a normal form single wave model; Mar. 2013.

Balmforth, N.J. et al. "Pattern formation in Hailtonian systes with continuous spectra; a normal-form single-wave model." In: arXiv preprint arXiv: 1303.0065. Mar. 1, 2013 from https://arxiv.org/pdf/1303.0065.pdf downloaded Aug. 10, 2016.

Behrens, T.E.J. et al., Probabilistic diffusion tractography with multiple fibre orientations: What can we gain?; NeuroImage vol. 34 (2007) pp. 144-155.

Bista, Sujal et al., Visualization of Brain Microstructure through Spherical Harmonics Illumination of High Fidelity Spatio-Angular Fields; IEEE Trans Vis Comput Graph, Dec. 2014; 20(12):2416-2525.

Burda, Z. et al., The various facets of random walk entropy, presented at the 22nd Marian Smoluchowski Symposium on Statistical Physics, Zakopane, Poland, Sep. 12-17, 2009, 40 pages.

Campbell, Jennifer S.W. et al., Diffusion Imaging of White Matter Fibre Tracts, Thesis submitted to McGill University, Nov. 8, 2004, Montreal, Canada, copyright Jennifer Campbell, 2004, 183 pages.

Cargo, M. Multidimensional quantum normal forms, Moyal star product and torus quantization, Jul. 14, 2005.

Cargo, Matthew et al., "Multidimensional quantum normal forms, Moyal star product, and torus quantization," In arXiv.math-ph/0507032v1, Jul. 14, 2005 [online] [retrieved on Mar. 16, 2017].

Chang, Ping et al., "Predictability of Linear Coupled Systems. Part I: Theoretical Analyses" Journal of Climate, Apr. 2004, p. 1474-1486.

Chung, Moo K. et al., Encoding cortical surface by spherical harmonics, Statistica Sinica vol. 18 (2008), 1269-1291.

Descoteaux, Maxime et al., Deterministic and probabilistic Q-Ball tractctography: from diffusion to sharp fiber distributions, No. 6273, Aug. 2007, Theme BIO, 36 pages.

Enrvik, Aron, 3D visualization of weather radar data, Thesis project in computer graphics at Linkoping University, Linkoping, Jan. 2002, LITH-ISY-EX-3252-2002, 92 pgs.

Frank, Lawrence R. et al., Information pathways in a discorded lattice, Physical Review, E89, 032142 (2014), 11 pgs.

Galinsky, Vitaly L., et al., A Unified Theory of Neuro-MRI Shows Scale-Free Nature of Connectivity Modes, Neural Computation 29, 1441-1467 (2017).

Galinsky, Vitaly L. et al. "Simultaneous Multi-Scale Diffusion Estimation and Tractography Guided by Entropy Spectrum Pathways," IEEE Transactions on Medical Imaging, Dec. 18, 2014.

Galinsky, Vitaly L. et al., Automated segmentation and shape characterization of volumetric data, NeuroImage vol. 92 (2014) pp. 156-168.

Goncalves, Vitor, Interaction and visualization techniques for volumetric data of various scalar modalities: integration of visualization and interaction, Electronica E. Telecomunicacoes, vol. 5, No. 3, Jun. 2011, pp. 344-351.

Huang, Heng, et al., Functional analysis of cardiac MR images using SPHARM modeling, Proc. SPIE 5747, Medical Imaging 2005: Image Processing, May 5, 2005, 1384; doi:10.1117/12.595954.

Le Bihan, Denis, Diffusion, Confusion and Functional MRI, NeuroImage, 2011, doi: 10.1016/j.neuroimage.2011.09.058, 6 pages.

Lu, Meng, et al. Snake-based brain white matter fiber reconstruction, Bio-Medical Materials and Engineering vol. 24 (2014) pp. 2945-2953.

Miller, Michael I. et al., "Collaborative Computational Anatomy: An MRI Morphometry Study of the Human Brain Via Diffeomorphic Metric Mapping", Human Brain Mapping, 2009, vol. 30., pp. 2132-2141.

Mukherjee, P. et al., Diffusion tensor MR imaging and fiber tractography: technical considerations, AJNR Am J. Neuroradiol vol. 29, May 2009, pp. 843-852.

Mukherjee, P. et al., Diffusion tensor MR imaging and fiber tractography: theoretic underpinnings, AJNR Am J. Neuroradiol vol. 29, Apr. 2008, pp. 632-641.

PCT/US2014/055712, International Search Report / Written Opinion dated Dec. 8, 2014, 15 pages.

PCT/US2016/030446, International Search Report and Written Opinion, dated Aug. 8, 2016, 15 pages.

PCT/US2016/030446, Written Opinion dated Aug. 8, 2016, 12 pages.

PCT/US2017/015173 International Search Report and Written Opinion dated Apr. 12, 2017, 9 pages.

PCT/US2018/021235; International Search Report and Written Opinion dated Jul. 10, 2018; 9 pages.

Peters, J.F., et al., Classification of meteorological volumetric radar data using rough set methods, Pattern Recognition Letters, vol. 24 (2003) pp. 911-920.

Schoelkopf, Bernhard et al. Nonlinear Component Analysis as a Kernel Eigenvalue Problem, Neural Computation, 10,1299-1319 (1998).

Senjem, Matthew L., et al., Comparison of different methodological implementations of Voxel-based morphometry in neurodegenerative disease, Neuroimage vol. 26(2), Jun. 2005, pp. 600-608.

Setsompop, K et al., (2013), Pushing the limits of in vivo diffusion MRI for the Human Connectome Project; NeuroImage, vol. 80, Oct. 15, 2013; pp. 220-233.

Shaw, Christopher D., et al., Real-time weather data on terrain, Proc. SPIE 4368, Visualization of Temporal and Spatial Data for Civilian and Defense Applications, Aug. 23, 2001 8 pages.

(56) References Cited

OTHER PUBLICATIONS

Sinatra, Roberta, et al., Maximal-entropy random walks in complex networks with limited information, Physical Review vol. 83, 030103(R), 2011, 4 pages.
Styner, Martin, Statistical shape analysis of brain structures using SPHARM-PDM, Insight Journal, MICCAI 2006 Opensource Workshop, 7 pages.
Tournier, Jacques-Donald, et al., Diffusion tensor imaging and beyond, Magn Reson Med. vol. 65(6), Jun. 2011, pp. 1532-1556.
Galinsky, Vitaly L. et al., Joint Estimation of Effective BrainWave Activation Modes using EEG/MEG Sensor Arrays and Multi-modal MRI Volumes, Neural Computation 30, 1725-1749 (2018).

\* cited by examiner

JOINT ESTIMATION DIFFUSION IMAGING (JEDI)

RELATED APPLICATIONS

This application claims the benefit of the priority of U.S. Provisional Application No. 62/857,185, filed Jun. 4, 2019, which is incorporated herein by reference in its entirety

GOVERNMENT RIGHTS

This invention was made with government support under Grant No. MH096100 awarded by the National Institutes of Health and Grant No. DBI1147260 awarded by the National Science Foundation. The government has certain rights in the invention.

BACKGROUND

The sensitivity of diffusion weighted MR imaging (dMRI) methods to tissue microstructure continues to tantalize the research and clinical community with its promise of quantitative characterization of both local tissue microstructure through the analysis of intravoxel diffusion anisotropy and global tissue connectivity via the reconstruction of inter-voxel fiber pathways (i.e., tractography). Nevertheless, the problem of tissue heterogeneity continues to plague current standard dMRI methods, limiting its ability to provide reliable estimates of both local and global tissue properties, thus ultimately limiting its utility in both research and clinical applications.

Diffusion tensor imaging (DTI), with its sensitivity to microscopic variations in diffusion anisotropy (DA) in neural tissues, has generated great interest in both basic neuroscience research and clinical applications as a method that offers the potential for the non-invasive assessment of the status of neural tissue architecture. The existing art in the field falls into two categories: analysis of single pair of pulsed field gradient (sPFG) data for detecting macroscopic diffusion anisotropy and global connectivity in brain white matter (WM), which comprise the standard DTI methods, and double pulsed field gradient (dPFG) analysis methods for detecting microscopic anisotropy for brain gray matter (GM). Standard art in both methods is error prone due to complications with tissue fiber heterogeneity. The GO-ESP method disclosed in U.S. Pat. No. 9,654,212 of the present inventors was developed to overcome the deficiencies in existing DTI (i.e., sPFG) methods and was shown to provide more robust and accurate estimates in WM.

As a first step for addressing the shortcomings of existing methods for analyzing data acquired using single pulsed field gradient (sPFG) methods—the standard diffusion tensor imaging (DTI) technique—we recently demonstrated that reformulation of the problem in probabilistic (i.e., Bayesian) terms with prior information consisting of neighboring diffusion information encoded using the theory of entropy spectrum pathways ("ESP"), combined with a geometrical optics approach to tractography, provided a robust and reliable method ("GO-ESP"), both disclosed in U.S. Pat. No. 9,654,212, which is incorporated herein by reference. This approach is capable of estimating local voxel anisotropy and global connectivity, even in the presence of voxels that contain complex multiple fibers distributions.

The connectivity information can be augmented with high resolution anatomical information (i.e., spatial organization of tissue types) using the method of joint estimation with space-time entropy regularization ("JESTER") disclosed by the present inventors in U.S. Patent Publication No. 2020/0051255 (incorporated herein by reference). The resulting combination of multi-modality data enables resolution of fiber crossing angles as small as 8° and allowed us to discern that the global structure of white matter pathways appeared to be a lamellar vector field (See, V. Galinsky and L. Frank, *Neural Computation* 2016, 28(11):2533-2556).

However, while the inventors' previously disclosed methods were able to overcome some of the major limitations of the prior art, they are still predicated on the existence of some average diffusion anisotropy over the entire voxel, so-called "macroscopic anisotropy." This property is characteristic of voxels containing only white matter (WM) whose long neural bundles typically traverse through voxels and, thus, provide a coherent directionality of the diffusion weighted signal when averaged over an entire voxel, even though the individual axons are significantly smaller in cross section ($\approx 50$ $\mu m^2$) than the typical imaging voxel ($\approx 2$ $mm^3$). However, as has been discussed in the literature, sPFG methods are ultimately limited in the presence of voxels whose internal tissue structure is so complex as to render their macroscopic anisotropy negligible, with gray matter (GM) voxels being the most important example. Nevertheless, voxels with no macroscopic anisotropy may still possess anisotropy on sub-voxel spatial scales (referred to as "microscopic anisotropy"). In reality, due to the highly heterogeneous nature of brain tissues, partial volume effects resulting in voxels with both GM and WM, and the infiltration of coherent neuronal fiber pathways into GM, the boundaries between these two situations is necessarily blurred. These idealized views of WM and GM serve as a useful dividing line for discussion.

The inability of sPFG methods to detect microscopic anisotropy has led in recent years to a line of inquiry into more complex acquisitions that are sensitive to this quantity. By applying multiple q-space encoding gradient pairs at different orientations and time separation within a single echo time, the MR signal can be sensitized to the correlation of water motion during consecutive blocks, and thus to specifically the restricted diffusion components of the microscopic anisotropy. These are generally referred to as "multiple wave vector" methods. The simplest (and most ubiquitous) implementation is two bipolar pairs, with different relative amplitudes and diffusion encoding directions and is referred to as "double PFG" (dPFG). Extensive work has been done in recent years to characterize the microscopic anisotropy to which dPFG methods are sensitive, particularly in gray matter. Significant work is ongoing in implementing DFPG sequences on human scanners for clinical applications.

One important practical aspect of dPFG methods is that they can be sensitive to restricted diffusion at diffusion wavelengths that are long compared to the dimensions of the restrictions. As a result, they require only modest diffusion gradients and are, therefore, attractive for potential clinical applications. To a large extent, research in these methods has fallen into two camps: (1) very detailed mathematical analysis of the signal in idealized geometries that lend themselves to analytical solutions, but are perhaps somewhat removed from the complexities of realistic tissue architectures; and (2) simplified averaged properties derived from low order forms of these complex idealized models. In fact, analytical models for more realistic tissue microstructures would be difficult to obtain, and alternative approaches are needed.

SUMMARY OF THE INVENTION

Current standard neuroimaging protocols include collection of high resolution anatomical (HRA) data and sPFG (i.e., DTI) data using a standard pulse sequence. From these data, estimates of local anisotropy and global connectivity are derived via post-processing algorithms. The inventive methods use standardly acquired data along with data from an additional standard dPFG acquisition, which can be acquired with the same pulse sequence, making it relatively easy to implement. These data are then analyzed off-line to provide more detailed local anisotropy and global connectivity estimates and maps. The inventive method and system for estimates local diffusion anisotropy and global tractography within neural architecture from diffusion weighted magnetic resonance image (dMRT) data by integrating a first dataset comprising standard single pulsed field gradient (sPFG) dMRI data with a second dataset comprising double pulsed field gradient (dPFG) dMRT data into a common coordinate system with the same spatial resolution. The resulting image includes integrated macroscopic and microscopic anisotropy and global tractography within the target volume.

In one aspect of the invention, the sPFG and dPFG data are combined using JESTER (see U.S. Publ. No. 2020/0051255), which uses spherical wave decomposition (SWD) (U.S. Pat. No. 10,297,022), and the novel registration method (SymReg-ESP) disclosed in International Publ. No. WO 2017/132403 to integrate HRA, sPFG, and dPFG data into a common coordinate system with the same spatial resolution. The GO-ESP analysis for diffusion estimation, which is based on the method of entropy spectrum pathways (ESP) (U.S. Pat. No. 9,645,212) is combined with a novel DiTSI approach for dPFG analysis (disclosed herein) into a joint estimation method referred to as "JEDI": Joint Estimation Diffusion Imaging. In the JEDI method, joint estimation for the parameters in each of these modalities is performed using a novel joint coupling and estimation scheme that generates more detailed and accurate estimates and maps of neural tissue status, architecture, and connectivity. The disclosures of each of the referenced patents and patent publications are incorporated herein by reference.

In one embodiment, a new method is provided for combining standard single pulsed field gradient (sPFG) diffusion weighted magnetic resonance (dMRI) data used for estimation of local macroscopic diffusion anisotropy and global tractography with double pulsed field gradient (dPFG) dMRI data used for estimation of local microscopic diffusion anisotropy into a single estimation scheme that provides more accurate estimates of both local diffusion anisotropy and global connectivity. This method combines previously-disclosed methods for morphological shape analysis and segmentation (SWD), for simultaneous local diffusion estimation and global tractography (GO-ESP), and a new method called Diffusion Tensor Subspace Imaging (DiTSI) for dPFG analysis, as well as a fast and accurate approach for non-linear registration between modalities (SYMREG), combined using the joint estimation procedure for integrating multi-modal data (JESTER). This joint analysis method is capable of extracting new levels of information that is not achievable from sPFG or dPFG modalities alone. The new theoretical dPFG analysis (DiTSI), combined with a new theoretical framework for joint sPFG+dPFG analysis (JEDI) within the probabilistic framework of JESTER allow construction of quantitative diffusion anisotropy and connectivity measures previously unattainable.

The additional information provided to the inventors' previously-disclosed GO-ESP analysis by the dPFG data via DiTSI is used to augment the sPFG data resulting in a significant improvement in the estimation of the tissue microstructure and tractography compared with those obtained using standard analysis. This integrated analysis method for the joint estimation of both microscopic and macroscopic anisotropy provides for more robust characterization of whole brain local (voxel) anisotropy and global connectivity (tractography). The JEDI approach compares favorably to standard DTI methods in terms of the well-known problem that standard sPFG methods have in discerning the fibers curving into the gray matter as they feed into the gyral blades, called the "gyral bias" problem.

In one aspect of the invention, a method for estimating local diffusion anisotropy and global tractography within neural architecture data includes: acquiring within a computer processor a first dataset and a second dataset from an imaging system configured to generate diffusion weighted magnetic resonance (dMRI) data for a target volume, the first dataset comprising single pulsed field gradient (sPFG) data and the second dataset comprising double pulsed field gradient (dPFG) data; using the computer processor, processing the first and second datasets separately or in parallel by: applying a spherical wave decomposition (SWD) algorithm to the first dataset to analyze morphological shape and segmentation for the target volume; applying a geometric optics-entropy spectrum pathways (GO-ESP) algorithm to the first dataset to identify ranked pathways between locations to detect macroscopic anisotropy and global tractography within the target volume; computing a weighted spin density function from the second dataset, wherein the weighted spin density function is 6-dimensional comprising a voxel coordinate and two 3-dimensional diffusion displacement coordinates on a radial grid defined within the target volume; defining a coupling matrix from the weighted spin density function to determine angular and radial variances within the second dataset, wherein the angular and radial variances are associated with diffusion properties for detecting microscopic anisotropy within the target volume; using the computer processor, integrating the detected macroscopic anisotropy and global tractography from the first dataset with the detected microscopic anisotropy from the second dataset using symplectomorphic registration (SYMREG) and joint estimation with space-time regularization (JESTER); and generating an output to a display device in communication with the computer processor, the output comprising an image corresponding to integrated macroscopic and microscopic anisotropy and global tractography within the target volume.

The weighted spin density function is a function of a voxel coordinate and two 3-dimensional displacement coordinates within the second dataset and may be constructed by determining angular standard deviation averaged over all radial dependencies to represent different angular variations of the spin density function and radial standard deviation averaged over all angular dependencies to represent different spatial scales of the weighted spin density. Additional steps may include generating a matrix of angular variances from the angular standard deviations and generating a matrix of radial variances from the radial standard deviations and mapping each matrix to a scalar quantity for visualization.

The first dataset and the second dataset may be acquired from the same dMRI pulse sequence.

In another aspect of the invention, a method for estimating local diffusion anisotropy and global tractography within neural architecture from diffusion weighted magnetic resonance image (dMRI) data involves using a computer processor to: integrate a first dataset comprising standard single pulsed field gradient (sPFG) dMRI data with a second dataset comprising double pulsed field gradient (dPFG) dMRI data, each dataset obtained for a target volume, into a common coordinate system with a same spatial resolution; and generate an output to a display device in communication with the computer processor, the output comprising an image corresponding to integrated macroscopic and microscopic anisotropy and global tractography within the target volume. Prior to integrating, the first dataset is processed by applying morphological shape analysis and segmentation (SWD) for estimating simultaneous local diffusion and determining global tractography by determining entropy spectrum pathways combined with geometrical optics (GO-ESP) to estimate local voxel anisotropy and global connectivity. Also prior to integrating, the second dataset is processed by computing a weighted spin density function, wherein the weighted spin density function is 6-dimensional comprising a voxel coordinate and two 3-dimensional diffusion displacement coordinates on a radial grid defined within the target volume. Integrating may be achieved using joint estimation in space-time regularization (JESTER) and symplectomorphic registration (SYMREG) to perform nonlinear registration between modalities. The first dataset and the second dataset are acquired from the same dMRI pulse sequence.

In another aspect of the invention, a system for estimating local diffusion anisotropy and global tractography within neural architecture data includes a memory storing computer-executable instructions; a processor in communication with the memory and configured to execute the computer-executable instructions to perform: acquiring a first dataset and a second dataset from an imaging system configured to generate diffusion weighted magnetic resonance (dMRI) data for a target volume, the first dataset comprising single pulsed field gradient (sPFG) data and the second dataset comprising double pulsed field gradient (dPFG) data; processing the first and second datasets separately or in parallel by: applying a spherical wave decomposition (SWD) algorithm to the first dataset to analyze morphological shape and segmentation for the target volume; applying a geometric optics-entropy spectrum pathways (GO-ESP) algorithm to the first dataset to identify ranked pathways between locations to detect macroscopic anisotropy and global tractography within the target volume; computing a weighted spin density function from the second dataset, wherein the weighted spin density function is 6-dimensional comprising a voxel coordinate and two 3-dimensional diffusion displacement coordinates on a radial grid defined within the target volume; defining a coupling matrix from the weighted spin density function to determine angular and radial variances within the second dataset, wherein the angular and radial variances are associated with diffusion properties for detecting microscopic anisotropy within the target volume; integrating the detected macroscopic anisotropy and global tractography from the first dataset with the detected microscopic anisotropy from the second dataset using symplectomorphic registration (SYMREG) and joint estimation with space-time regularization (JESTER); and generating an output to a display device in communication with the computer processor, the output comprising an image corresponding to integrated macroscopic and microscopic anisotropy and global tractography within the target volume. The weighted spin density function is a function of a voxel coordinate and two 3-dimensional displacement coordinates within the second dataset and may be constructed by determining angular standard deviation averaged over all radial dependencies to represent different angular variations of the spin density function and radial standard deviation averaged over all angular dependencies to represent different spatial scales of the weighted spin density. Further steps may include generating a matrix of angular variances from the angular standard deviations and generating a matrix of radial variances from the radial standard deviations and mapping each matrix to a scalar quantity for visualization. The first dataset and the second dataset may be acquired from the same dMRI pulse sequence.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A shows that first component of the radial standard deviation $\sigma(R_1^{(1)}, R_2^{(1)})$ in a normal human; and FIG. 4B shows the angular standard deviation $\sigma_\Omega$ in a normal human.

FIG. 14A is a coronal section through the superior temporal gyms; FIG. 14B is a higher magnification view of the lateral aspect of FIG. 13A.

DETAILED DESCRIPTION OF EMBODIMENTS OF THE INVENTION

The inventive method leverages the inventors' previously disclosed analytical tools to develop a general approach for dMRI analysis that incorporates both sPFG and dPFG data to provide joint estimation of both microscopic and macroscopic anisotropy for more robust characterization of whole brain local (voxel) anisotropy and global connectivity (tractography). This reformulation of general neuro-MRI analysis methodology is aimed at providing a generic, logically consistent framework for inference of physical parameters and structures from complex multi-modal noisy multivariate data. The following description details the systems, steps and algorithms employed in the inventive scheme as well as providing examples of applications of the method to data.

Figure 15:
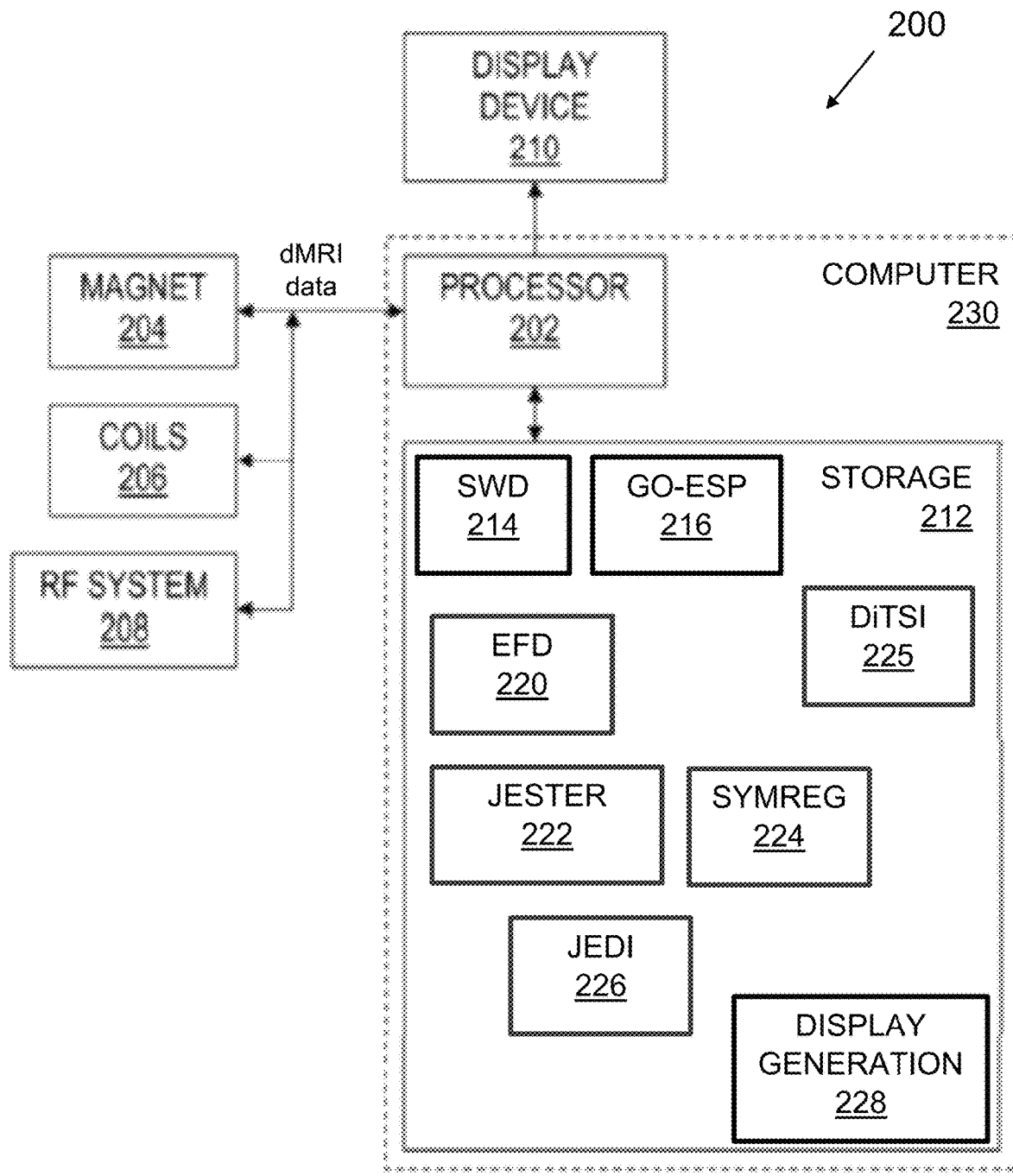
FIG. 15 is a block diagram of an exemplary imaging and computing system in accordance with various embodiments of the invention.

FIG. 15 is a block diagram of an exemplary magnetic resonance (MR) imaging system 200 in accordance with various embodiments. The system 200 includes a main magnet 204 to polarize the sample/subject/patient; shim coils 206 for correcting inhomogeneities in the main magnetic field; gradient coils 206 to localize the MR signal; a radio frequency (RF) system 208 which excites the sample/subject/patient and detects the resulting MR signal; and one or more computers 230 to control the aforementioned system components.

A computer 230 of the imaging system 200 comprises a processor 202 and storage 212. Suitable processors include, for example, general-purpose processors, digital signal processors, and microcontrollers. Processor architectures generally include execution units (e.g., fixed point, floating point, integer, etc.), storage (e.g., registers, memory, etc.), instruction decoding, peripherals (e.g., interrupt controllers, timers, direct memory access controllers, etc.), input/output systems (e.g., serial ports, parallel ports, etc.) and various other components and sub-systems. The storage 212 includes a computer-readable storage medium.

Software programming executable by the processor 202 may be stored in the storage 212. More specifically, the storage 212 contains software instructions which, when executed by the processor 202, cause the processor 202 to acquire diffusion weighted magnetic resonance (dMRT) data (sPFG and dPFG) for the region of interest ("ROI") and process it. sPFG data is processed by spherical wave decomposition (SWD) module (SWD module 214) for shape analysis. Entropy spectrum pathways (ESP) and ray tracing are performed using a geometric optics tractography algorithm (GO-ESP module 216) for estimation of local diffusion anisotropy and global connectivity. Separately, the dPFG data is analyzed by DiTSI module 225. The results of the analysis of the sPFG data and the dPFG data are combined via joint estimation in space-time regularization (JESTER) (JESTER module 222) (which employs SWD and is an extension of EFD (EFD module 220), and symplectomorphic registration (SYMREG module 224), which provides non-linear registration between modalities to integrate the data into a common coordinate system with the same spatial resolution. The JEDI module 226 then applies joint coupling and estimation to combine the data into an integrated image. Display generation module 228 generates integrated images of the ROI for graphical display (e.g., on display device 210, which may be any device suitable for displaying graphic data). More particularly, the software instructions stored in the storage 212 cause the processor 202 to process the dMRI data to display an integrated image of macroscopic diffusion anisotropy and global connectivity in brain white matter (WM) and the microscopic anisotropy of brain gray matter (GM), providing accurate estimates and maps of neural tissue status, architecture and connectivity in the ROI. This integrated approach enables a comprehensive view of the brain's structure-function relations.

Additionally, the software instructions stored in the storage 212 may cause the processor 202 to perform various other operations described herein. In some cases, one or more of the modules may be executed using a second computer of the imaging system. (Even if the second computer is not originally or initially part of the imaging system 200, it is considered in the context of this disclosure as part of the imaging system 200.) In this disclosure, the computers of the imaging system 200 are interconnected and configured to communicates with one another and perform tasks in an integrated manner. For example, each computer is provided access the other's storage.

In other cases, a computer system (similar to the computer 230), whether being a part of the imaging system 200 or not, may be used for post-processing of diffusion MRI data that have been acquired. In this disclosure, such a computer system comprises one or more computers and the computers are interconnected and are configured for communicating with one another and performing tasks in an integrated manner. For example, each computer has access to another's storage. Such a computer system may comprise a processor and a computer-readable storage medium (CRSM). The CRSM contains software that, when executed by the processor, causes the processor to obtain diffusion magnetic resonance (MRI) data in region of interest (ROI) in a patient and process the data by performing spherical wave decomposition (SWD), entropy spectrum pathway (ESP) analysis and applying geometric optics (GO) algorithms to execute ray tracing operations to define fiber tracts for display on a display device.

Characterizing the dPFG Signal in a Single Voxel (DiTSI)

The dPFG signal $W(r, q_1, q_2)$ measured in both r (the voxel coordinate) and q space ($q=\gamma G \delta$, with G and $\delta$ being the strength and duration of the diffusion-encoding gradient and $\gamma$ the gyromagnetic ratio of protons, can be expressed in terms of the weighted spin density function $\Phi(r, R_1, R_2)$ in the diffusion displacement coordinate R, defined as a change in particle position over time t, $R=r(t_0+t)-r(t_0)$ as $$W(r,q_1,q_2) = \iint dR_1 dR_2 \Phi(r,R_1,R_2) e^{-iq_1 \cdot R_1} e^{-iq_2 \cdot R_2} \quad (1)$$

To find an expression for the spin density function $\Phi(r, R_1, R_2)$, we use the plane wave expansion in spherical coordinates with $q=q\hat{q}$ and $R=R\hat{R}$ where $q=\|q\|$ and $R=\|R\|$, $$e^{iq \cdot R} = 4\pi \sum_{l=0}^{\infty} \sum_{m=-l}^{l} i^l j_l(qR) Y_l^{m*}(\hat{q}) Y_l^m(\hat{R}), \quad (2)$$

where $j_l(qR)$ is the spherical Bessel function of order l and $Y_l^m(\hat{q})=Y_l^m(\Omega_{\hat{q}})=Y_l^m(\theta_q,\phi_q)$ is the spherical harmonic with $\theta_q$ and $\phi_q$ being the polar and azimuthal angles of the vector q, and similarly for the vector R.

We can rewrite Equation (1) as $$W(r, q_1, q_2) = \quad (3)$$

$$(4\pi)^2 \iint dR_1 dR_2 \Phi(r, R_1, R_2) \times \sum_{l_1=0}^{\infty} \sum_{m_1=-l_1}^{l_1} i^{l_1} j_{l_1}(q_1 R_1) Y_{l_1}^{m_1*}(\hat{q}_1)$$

$$Y_{l_1}^{m_1}(\hat{R}_1) \times \sum_{l_2=0}^{\infty} \sum_{m_2=-l_2}^{l_2} i^{l_2} j_{l_2}(q_2 R_2) Y_{l_2}^{m_2*}(\hat{q}_2) Y_{l_2}^{m_2}(\hat{R}_2)$$

The spin density function $\Phi(r, R)$ depends on voxel coordinate r and the dynamic (or diffusion) displacement coordinate R, defined as a change in particle position over time t, $R=r(t_0+t)-r(t_0)$. It can be expressed, using the spherical wave decomposition (SWD) in the form $$\Phi(r, R_1, R_2) = (4\pi)^2 \quad (4)$$

$$\sum_{l_1=0}^{\infty} \sum_{m_1=-l_1}^{l_1} \sum_{l_2=0}^{\infty} \sum_{m_2=-l_2}^{l_2} i^{l_1} i^{l_2} Y_{l_1}^{m_1}(\hat{R}_1) Y_{l_2}^{m_2}(\hat{R}_2) s_{l_1,m_1,l_2,m_2}(r, R_1, R_2)$$

where $$s_{l_1,m_1,l_2,m_2}(r,R_1,R_2) = \iint W(r,q_1,q_2) j_{l_1}(q_1 R_1) j_{l_2}(q_2 R_2) Y_{l_1}^{m_1*}(\hat{q}_1) Y_{l_2}^{m_2*}(\hat{q}_2) dq_1 dq_2 \quad (5)$$

The spherical Bessel function $j_l(qR)$ of order l characterizes radial variations while the spherical harmonics $Y_l^m(\hat{q})=Y_l^m(\Omega_{\hat{q}})=Y_l^m(\theta_q,\phi_q)$ of order l characterizes the angular variation.

Unlike standard sPFG analysis methods in which the spin density function is 3-dimensional, here the spin density function $\Phi(r, R_1, R_2)$ is 6-dimensional (in displacement coordinate space), being a function of both 3-dimensional displacement coordinates $R_1$ and $R_2$. The spin density Equation (4) can be reconstructed directly numerically at multiple radial and angular scales. Computational subspaces defined by the ranges of radial and angular resolution provide information on these different scales, and thus form the basis of an important aspect of the inventive method: "Diffusion Tensor Subspace Imaging", or ("DiTSI"). However, the high dimensionality of $\Phi$ makes it a complicated quantity for describing voxel characteristics. Therefore, it is useful from a practical perspective to construct two quantities of lower dimensionality but physical significance: the radial and angular standard deviations of $\Phi$:

$$\sigma_{R_1,R_2} \equiv \sigma(R_1, R_2) = \frac{1}{4\pi} \left( \iint d\Omega_1 d\Omega_2 [\Phi(r, R_1, R_2) - \bar{\Phi}_\Omega]^2 \right)^{1/2} \quad (6)$$

$$\sigma_{\Omega_1,\Omega_2} \equiv \sigma(\Omega_1, \Omega_2) = \frac{1}{R_{max}} \left( \iint dR_1 dR_2 [\Phi(r, R_1, R_2) - \bar{\Phi}_R]^2 \right)^{1/2} \quad (7)$$

where $\Omega=(\theta, \phi)$ and $\bar{\Phi}_R$ and $\bar{\Phi}_\Omega$ are radial and angular averages of the spin density function $$\bar{\Phi}_R(\Omega_1, \Omega_2) = \frac{1}{R_{max}^2} \iint dR_1 dR_2 \Phi(r, R_1, R_2) \quad (8)$$

$$\bar{\Phi}_\Omega(R_1, R_2) = \frac{1}{(4\pi)^2} \iint d\Omega_1 d\Omega_2 \Phi(r, R_1, R_2) \quad (9)$$

The angular standard deviation $\sigma_{\Omega_1,\Omega_2}$ gives the angular dependence of $\Phi$ averaged over all the radial dependencies and so is representative of the different angular variations of $\Phi$. The radial standard deviation $\sigma_{R_1,R_2}$ gives the radial dependence of $\Phi$ averaged over all the angular dependences and so is representative of the different spatial scales of $\Phi$.

The reconstruction of $\Phi$ in Equation (4) was developed using a fast Fourier transform based SWD and is governed by the following parameters: angular discretization $l_{max}$, radial discretization $n_{max}$, maximum order of the spherical harmonics $2L-1=L_{max}$, maximum order of the spherical Bessel functions $N=N_{max}$, and the grid size d. Both $R_1$ and $R_2$ are constructed on 3D grids of size d×d×d. The resulting computed spin density function $\Phi$ is thus a 6-dimensional quantity of size $\Phi \equiv \Phi(d, d, d, d, d, d)$ with $d^6$ elements. The discretization produces a radial variance $\sigma_{R_1,R_2}$ of dimensions N×N (i.e., the integration over the $L^2 \times L^2$ angular components leaves the N radial components for both $R_1$ and $R_2$). In the single voxel simulation below, N=11, so $\sigma_R$ is 11×11.

The dimensions of the angular variance $\sigma_{\Omega_1,\Omega_2}$ are $4L^2 \times 4L^2$ (i.e., the integration over the N×N radial components leaves the $4L^2$ angular components for both $\Omega_1$ and $\Omega_2$). However, since $\Omega=\{\theta, \phi\}$, it is really of dimensions (2L×2L×2L×2L). In the single voxel simulation below, L=9, so $\sigma_{\Omega_1,\Omega_2}$ is of dimensions (18×18×18×18).

Given the emphasis of recent research on developing explicit models for diffusion tissues, it is worth elaborating on the fact that no tissue model is used in this framework, therefore it is not necessary to fit or estimate single or multi parametric diffusion properties of the underlying tissue variety, nor do we calculate any estimation for the averaged diffusion length. The reconstruction using n spherical Bessels on a radial grid simply assumes that $q_{min} R_{max} \sim 1$, hence $R_{max} \sim 1/q_{min} \sim n/q_{max}$. This estimate should provide more or less reasonable values for our choice of the size of radial grid, taking in account that the maximum b value is often chosen from practical consideration to be $b_{max} ADC \sim 1$. However, we emphasize that the radial grid is not fixed and the framework allows to select any feasible/appropriate radial and angular sizes and/or resolutions.

The important point is that we do not assume any behavior of the q-dependent signal beyond what is measured. We choose an R grid that roughly covers a region from $\sim 1/q_{max}$ to $1/q_{min}$ while only using a limited number of grid points in between since the relatively sparse radial sampling of the few acquired "shells" is too limited to expect that a very accurate R behavior can be restored. The 1/q behavior at large q will create most of the problems restoring $\Phi$-functions at small $R<1/q_{max}$, but actually that issue is of little practical concern. Given the rather sparse sampling in q, for tractography one does not need to have an extremely accurate estimate of $\Phi(R)$ at $R<R_0\sim 1/q_{max}$. It, therefore, seems to be of little practical value to construct explicit bases that best represent the signal from highly idealized models (such as infinitely narrow sticks) on only a few grid points and then demonstrate that as $R\rightarrow 0$ the models behaves badly.

In the inventive approach, all that is required is to calculate coupling matrix $Q_{ij}$ which involves an integral of $\Phi(R)$ over R under the assumption of bounded $\Phi(R)$ and recognize that the error due to large q truncation of this integral will be approximately. $\int_{R<R_0} \Phi(R) R^2 dR$, and thus will rapidly go to zero as $q_{max} \sim 1/R_0$ increases. In fact, this is true even if one does choose to use a singular propagator, as the integrals of the type used in the coupling matrix $Q_{ij}$ (or in the $\sigma$'s) are well defined. For example, if we assume that for the "infinitely-narrow stick" model the use of infinitely large domain of integration would be appropriate, this yields $$\int\int\int \frac{|r \cdot R|}{|r||R|}\Phi(r, R)dR^3 = \int\int\int \frac{|r \cdot R|}{|r||R|}\delta(X)\delta(Y)\frac{e^{-Z^2/4Dt}}{\sqrt{Dt}}dXdYdZ$$
$$= \frac{z}{|r|}\int \frac{e^{-Z^2/4Dt}}{\sqrt{Dt}}dZ,$$

which is a well-defined input to the coupling terms.

In this context, it is worth noting the relationship of the 1/q decay to modeling in practical applications. Our reconstruction of $\Phi$ involves 3D Fourier transforms which are a usual 1-D transform performed over any arbitrary direction in 3-D space. If one considers a Fourier coefficient $f_k$ from a function with a number of discontinuities taking 1-D Fourier transform along an arbitrary direction k (that is, assuming initially that x-axis is directed along $\hat{k}$ the input to $$\sim \frac{1}{k}\exp(-ikx)$$

for a single discontinuity at the x position. Then, for a distribution of discontinuities, $$f_k \sim \frac{1}{k}\int p(r)\exp(-ikx)dr^n, \quad (10)$$

where p(r) is (probability) density of a discontinuity at a position r. Power spectra $|f_k|^2 \equiv f_k^* f_k$ then will be $$|f_k|^2 \sim \frac{1}{k^2}\int\int p(r)p(r')\cos(k(x-x'))dr^n dr'^n. \quad (11)$$

The integral of probability density function $p(r)dr^n$ will not change with any stretching of the coordinate system (i.e., with $r \rightarrow kr$) hence this requires that $p(kr)k^n dr^n = p(r)dr^n$ and therefore $$|f_k|^2 \sim \frac{1}{k^2}\left[\left(\int p(r)\cos(x)dr^n\right)^2 + \left(\int p(r)\sin(x)dr^n\right)^2\right]. \quad (12)$$

As a choice of $\hat{k}$ direction was assumed arbitrary, we can write it in a vector form in the original coordinate system as $$|f_k|^2 \sim \frac{1}{|k|^2}\left[\left(\int p(r)\cos((\hat{k}\cdot r)\hat{k})dr^n\right)^2 + \left(\int p(r)\sin((\hat{k}\cdot r)\hat{k})dr^n\right)^2\right]. \quad (13)$$

hence the 2-D or 3-D (or n-D) Fourier coefficient amplitudes $|f_k|$ will decay as $1/|k|$. For this illustration we only included an isotropic spatial distribution p(r). A more realistic angular distribution would include some dependence on $\hat{s} \cdot \hat{k}$ integrated over all possible orientations $d^2\hat{s}$ (where $\hat{s}$ is a normal unit vector of discontinuity) and would result in an anisotropic $\hat{k}$-dependence, but again with the amplitudes decaying as $1/|k|$. This is valid for any Fourier transform irrespective of dimensionality n and irrespective of modeling—of dMRI, of diffusion, of tissue type, or other physical assumptions. It arises as soon as a transform of a function with discontinuities is encountered.

The radial and angular variances $\sigma_{R_1,R_2}$ and $\sigma_{\Omega_1,\Omega_2}$ characterize diffusion properties at different radial and angular scales, respectively, and as such contain a great deal of information. However, they are still multidimensional tensors and from a practical perspective it is useful to derive average quantities of lower dimensionality, particularly scalar quantities that can be easily overlaid on images to more easily discern spatial variations in diffusion properties that correspond to particular brain regions and tissue types. Averaging the radial variances matrix over all N×N radii provides the useful scalar quantity $$\langle \sigma_R \rangle = \int \sigma(R_1,R_2)dR_1 dR_2 \text{scalar} \quad (14)$$

The angular variance is a higher dimensional tensor and so there are two reductions that are useful:

$$\langle \sigma_{\Omega_1} \rangle = \int \sigma(\Omega_1,\Omega_2)d\Omega_2 \text{matrix}(2L \times 2L) \quad (15)$$

$$\langle \sigma_\Omega \rangle = \int \sigma(\Omega_1,\Omega_2)d\Omega_1 d\Omega_2 \text{scalar} \quad (16)$$

Equation (15) is an averaging over one set of angles $\Omega_2$ and reduces the $(2L)^4$ dimensional tensor to a matrix of dimension $(2L)^2$, which is easily visualized by mapping to a sphere, as described below. In the single voxel simulations below L=9 so $\langle \sigma_{\Omega_1} \rangle$ is of dimensions 18×18. Further reduction of this by averaging over the second set of angles $\Omega_1$ produces the scalar quantity, Equation (16), which is the average over all angles, and provides a scalar quantity easily visualized as an image overlay. This is the angular analog of the scalar quantity Equation (14) for the radial variance.

Joint Estimation (JEDI) Using Both sPFG and dPFG Data

Having provided a method (DiTSI) capable of detecting variations in microscopic anisotropy, and a robust method for detecting local diffusion macroscopic anisotropy and reconstructing highly complex fiber tracts (GO-ESP), a natural question is whether these methods can be combined to develop a method simultaneously sensitive to both macro- and microscopic anisotropy, and use this to better characterize complex tissue organization, and facilitate tractography through GM.

The approach used in the inventive scheme was to integrate DiTSI analysis from dFPG data with the GO-ESP scheme for analysis of sPFG data using the Joint Estimation using Entropy Regularization (JESTER) method (U.S. Patent Publication No. 2020/0051255), which is an extension of the Entropy Field Decomposition (EFD) method for analyzing spatiotemporal data disclosed in U.S. Patent Publ. 2018/0285687, which is incorporated herein by reference.

The JESTER approach, being based on a Bayesian framework, facilitates the joint estimation of all or any combination of MRI modalities and results in significantly more accurate estimates than existing methods. For example, tractography using GO-ESP combined with SWD from high resolution anatomical (HRA) data within JESTER results in an improvement of the anisotropy spatial resolution and the ability to resolve crossing fibers at or below 10 degree angular resolution. Calculating the eigenvector of the tractography connectivity matrix, which is referred to as Eigenmode Imaging (EMI), results in spatial resolution much higher than the original imaging modalities. Thus, a single estimation scheme can combine the unique information each modality provides about the same brain to significantly improve estimates of physical parameters.

Integration of the sPFG and dPFG analyses proceeds as follows: assuming that we have m=1, . . . , M different modalities $d^{(m)}$ with the coupling matrices $Q^{(m)}$ that all correspond to the same unknown signal s, we can construct an intermodality coupling matrix as the product of these coupling matrices for the individual modalities expressed in the ESP basis and registered to a common reference frame, which we denote as $\tilde{Q}^{(m)}$. That is, the joint coupling matrix is $Q^{(m)} = \Pi_m \tilde{Q}^{(m)}$. More specifically, the joint coupling matrix $Q_{ij}$ between any two space-time locations (i, j) can be written in the general (equivalent) form as $$\ln Q_{ij} = \sum_{m=1}^{M} \beta_{ij}^{(m)} \ln \tilde{Q}_{ij}^{(m)} \quad (17)$$

where the exponents $\beta^{(m)}$ can either be some constants or functions of data collected for different modalities $$\beta_{ij}^{(m)} = \beta^{(m)}(\tilde{d}_i, \tilde{d}_j), \tilde{d}_i = \{\tilde{d}_i^{(1)}, \ldots, \tilde{d}_i^{(M)}\} \quad (18)$$

where $\tilde{d}_i^{(m)}$ and $\tilde{Q}_{ij}^{(m)}$ represent, respectively, the data and the coupling matrix of the modality dataset m represented in the ESP basis and evaluated at locations $r_i$ and $r_j$ of a common reference domain R $$\tilde{d}_i^{(m)} = d^{(m)}(\psi^{(m)}(r_i)), \tilde{Q}_{ij}^{(m)} = Q^{(m)}(\psi^{(m)}(r_i), \psi^{(m)}(r_j)) \quad (19)$$

where $\psi^{(m)}: R \rightarrow X$ denotes a diffeomorphic mapping of m-th modality from the reference domain R to an acquisition space X. It should be noted that for multimodal coupling there are a variety of ways (of essentially arbitrary complexity) to appropriately introduce the coefficients β, as the arbitrary dependence in Equation (18) on the data suggests.

The form of the coupling depends upon the modality. For the HRA dataset, we define a simple intensity weighted nearest neighbors coupling matrix as $$Q_{ij}^H = e^{-\gamma_{ij}} = \begin{cases} d_i^H d_j^H & \text{nearest neighbors} \\ 0 & \text{not connected} \end{cases} \quad (20)$$

For DWI data, the GO-ESP procedure uses the spin density function Φ(r, R) expressed with the help of the spherical wave decomposition as $$\Phi(r, R) = 4\pi \sum_{l=0}^{\infty} \sum_{m=-l}^{l} i^l Y_l^m(\hat{R}) g_{lm}(r, R), \quad (21)$$

$$g_{lm}(r, R) \int W(r, q) j_l(qR) Y_l^{m*}(\hat{q}) dq. \quad (22)$$

The coupling matrix $Q_{ij}$ can be generated from the spin density function Φ(r, R) as as $$Q_{ij} = \frac{1}{2R_{max}^6} \int \cdots \int_{R_{min}}^{R_{max}} \frac{|(r_i - r_j) \cdot (R_1 - R_2)|}{|r_i - r_j||R_1 - R_2|} \quad (23)$$

$$[\Phi(r_i, R_1) + \Phi(r_j, R_2)] dR_1^3 R_2^3.$$

Practically, as the coupling matrix Qij only needs to be evaluated for 28 direct neighbors j of each voxel i and the R grid is relatively small, it is more convenient to replace cosine weighted 6 dimensional integration across all combinations of $R^3 \times R^3$ grid (with near zero input from off-the-line points) with just summation of components along the line between i and j neighbors and generate the symmetrized scale dependent coupling matrix $Q_{ij}^D$ as $$Q_{ij}^D(\ell) = Q_{ji}^D(\ell) = \frac{1}{2}[\Phi(r_i,(r_i-r_j)\ell) + \Phi(r_j,(r_j-r_i)\ell)] \quad (24)$$

where $\ell$ represents the dimensionless ratio of scales of dynamic displacement R to the spatial (voxel) scales r, $j_l(qR)$ is the spherical Bessel function of order 1 and $Y_l^m(\hat{q}) = Y_l^m(\Omega_{\hat{q}}) = Y_l^m(\theta_q, \phi_q)$ is the spherical harmonic with $\theta_q$ and $\phi_q$ being the polar and azimuthal angles of the vector q, and similarly for the vector R, and W(r, q) is the DW1 signal. It is worth noting that Equation (24) does not attempt to connect any scales and nothing is "implicitly" assumed about the functional dependence of the propagator. The propagator is only defined on a fixed grid from $R_{min} \sim 1/q_{max}$ to $R_{max} \sim 1/q_{min}$ and $\ell$ is introduced as a dimensionless line integration parameter along the ri–rj direction but in displacement (R) space (as there is no need to know the r dependence for the numerical integration).

JESTER extends the EFD procedure to incorporate information from multiple modalities by constructing coupling matrices $Q_{ij}^m$ that relate data from different modalities m at location ij to one another within a formal Bayesian framework. For the current problem, both the sPFG and dPFG data represent two modalities that can be estimated simultaneously by incorporating these single modality coupling matrices $Q_{ij}^H$ and $Q_{ij}^D$ in Equation (15) to generate the intermodality coupling matrix $Q_{ij}$. This can be extended to incorporate our DiTSI analysis for GM into our current form of JESTER which includes the GO-ESP method for WM diffusion anisotropy estimation and tractography. This is the basis of the inventive JEDI method. The details of coupling matrix expressions are given by Galinsky and Frank in *Neural Comput.* 2017; 29:1441-1467, which is incorporated herein by reference.

In order to incorporate the dPFG data into the GO-ESP method, the multidimensional spin density function $\Phi(r, R_1, R_2)$ generated by DiTSI can be naturally included in the JESTER estimation procedure by assuming the displacement grid R as a subvoxel extension of the position grid r. The new coupling matrix that incorporates the dPFG data is provided in Equation (25):

$$Q_{ij} = Q_{ji} = \frac{1}{2R_{max}^{12}} \int \cdots \int_{R_{min}}^{R_{max}} \frac{|(r_i - r_j) \cdot (R_1 + R_2 - R_3 - R_4)|}{|r_i - r_j||R_1 + R_2 - R_3 - R_4|} \cdot [ \qquad (25)$$
$$\Phi(r_i, R_1, R_2) + \Phi(r_j, R_3, R_4)]dR_1^3 dR_2^3 dR_3^3 dR_4^3.$$

Again, the grid is small, so the 12-dimensional integration for the nearest i-j neighbors need not be done. Instead, a precomputed table of summation along a set of $R_1$ and $R_2$ components of $\Phi(r, R1, R2)$ can be used to give the largest input to the neighbor direction vector.

The multidimensional structure of the spin-density function $\Phi(r, R_1, R_2)$ produces the subvoxel coupling term $Q_{ij}(r)$, which, when used in addition to directional line coupling of sPFG $\Phi_l(r)$ results, in significant improvement of fiber tractography. This is especially true for bundles going through difficult areas of single voxel fiber direction changes or bundle splits. The resulting joint GO-ESP DiTSI is the JEDI method.

EXAMPLES

The following examples apply the novel DiTSI and JEDI methods to simulated and actual data corresponding to brain images.

Example 1: Single Voxel Simulation

An illustrative example of DiTSI is provided by simulating the signal from a single voxel with structures composed of idealized WM and GM geometries. The voxel diffusion characteristics were constructed in a similar fashion as disclosed by Özarslan, et al., *J. Chem Phys.* 2009; 130: 104702 (incorporated herein by reference) by assuming that the voxel is discretized into p equal sections in each direction and thus $p^3$ cubic subvolumes (or "pores"), each of which contained a simple ellipsoidal diffusion profile characterized by a real symmetric 3×3 diffusion tensor characterized by the three principal eigenvectors and their associated eigenvalues $\{\lambda_1, \lambda_2, \lambda_3\}$. The simulation input allowed arbitrary manipulation of the relative eigenstructure of these ellipsoids, facilitating the generation of various "tissue" models. For illustrative purposes, mitigation of angular sampling discretization provides more informative examples and so a large number of unique diffusion angles (100) generated uniformly on a sphere were used, although the simulation program can also use any dPFG strategy such as those shown in FIG. 11. (Note that the sampling in the octahedron has orthogonal vectors while the cube does not.) For the dPFG simulation two b-values were used and the complete sampling is generated as the Cartesian product of the gradient pattern, resulting in 40 k samples. For the simulations shown below, p=6 giving a total of $6^3$=216 pores in the "voxel". For the acquisition parameters, we used a diffusion time $\Delta$=50 ms, width of diffusion gradients $\delta$=20 ms, and two shells with b=(2401, 4803)s/mm².

Note that sampling schemes show the acquisition gradient space q. The reconstruction is done in reciprocal sampling space R which can use different angular discretization grid that is not required to be the same as the acquisition grid. The reconstructions were run using the following parameters: angular discretization $l_{max}$=9, radial discretization $n_{max}$=10, spherical harmonics $L_{max}$=9, spherical Bessel $N_{max}$=11, grid size 13×13×13. The results are summarized in FIG. 1 and FIG. 2, which show a graphical description of the tissue models, the spin density function $\Phi(R)$ from a simulated sPFG acquisition, the average angular deviation $\langle \sigma_{\Omega_1} \rangle$, and the radial deviation $\sigma_R$ computed by DiTSI, demonstrating its ability to detect both radial and angular microscopic anisotropy.

Figure 1:
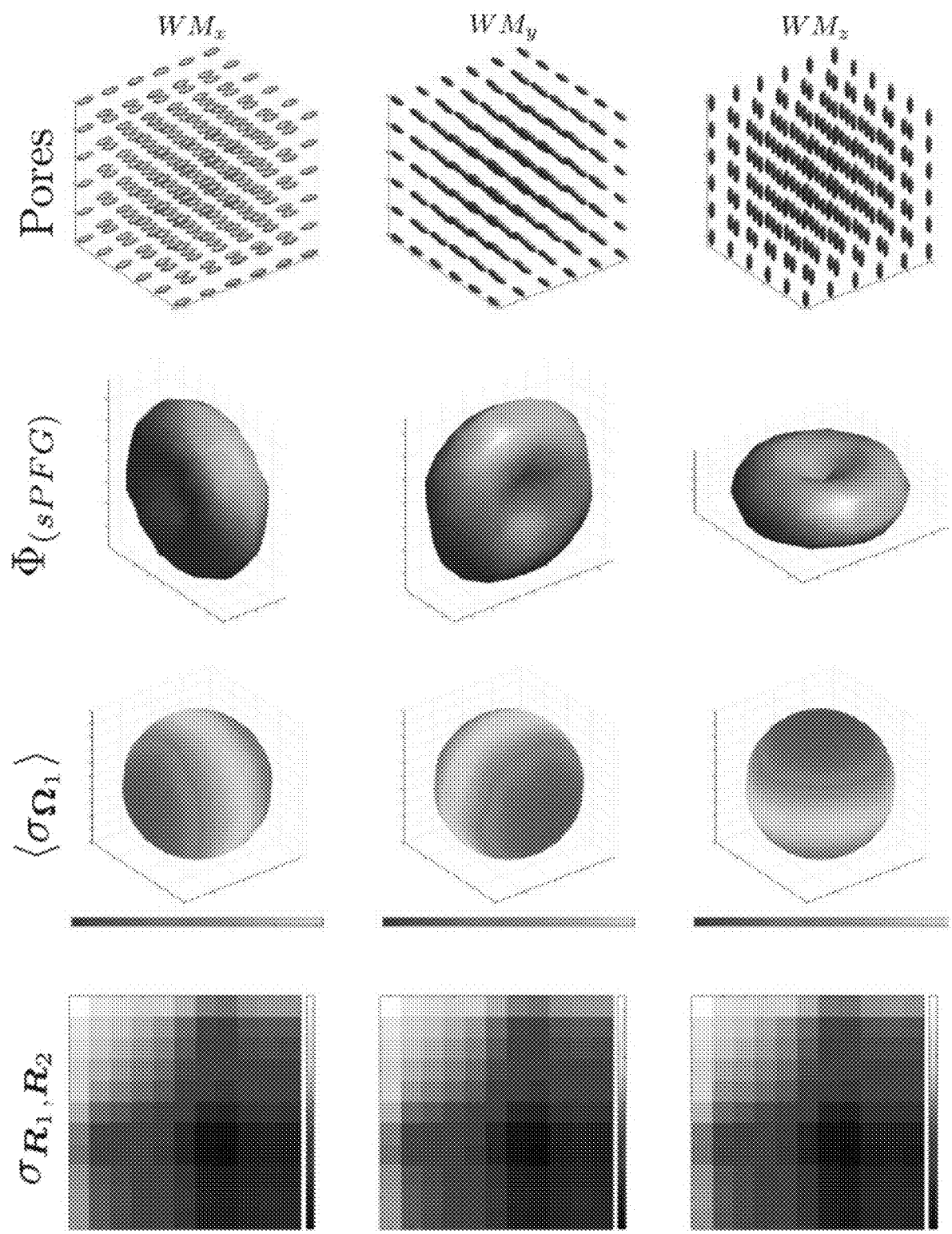
FIG. 1 illustrates a set of white matter (WM) tissue models in which all pores are identical with $(\lambda_1, \lambda_2, \lambda_3) = (1, 1, 10)$ where the top row shows example voxels with fibers along orthogonal axes (x, y, z); the second row shows spin density function $\Phi$ estimated from a simulated sPFG acquisition; the third row shows DiTSI results of angular variance $\langle \sigma_{\Omega_1} \rangle$ of size (2L×2L) mapped onto a sphere where L=9 is the maximum spherical harmonic order; and the fourth row provides the DiTSI results of full radial variance $\sigma_{R_1,R_2}$ with a pronounced peak at the origin $R_1=R_2$.

FIG. 1 shows the WM tissue model simulation results. All pores are identical with $\{\lambda_1, \lambda_2, \lambda_3\}$={1, 1, 10}. The top row shows three voxels with fibers along the orthogonal axes {x, y, z}. In Row 2, spin density function $\Phi$ is shown as estimated from a simulated sPFG acquisition and demonstrates the familiar shape characteristic of macroscopically averaged anisotropy to which sPFG is sensitive. Row 3 shows DiTSI results of the angular variance $\langle \sigma_{\Omega_1} \rangle$ (Equation 15) of size (2L×2L) mapped onto a sphere. These show an angular band of intensity consist with both the geometry of the underlying pores and with the sPFG estimates. Row 4 shows the DiTSI results of full radial variance $\sigma_{R_1,R_2}$ (Equation (6)) which has a pronounced peak at the origin $R_1 = R_2$.

The intensity pattern of $\sigma_{R_1,R_2}$ reveals an interesting and potentially useful new aspect of the DiTSI analysis. Note that the fall-off with larger radius is not monotonic but has peaks. This is most likely a result of both a limited range of eigenvalues used for the dPFG signal generation and a fixed sampling/discretization size used for the data acquisition and analysis. These results nonetheless demonstrate the ability of DiTSI to distinguish between different kinds of microstructure organization and possible development of more detailed metrics of tissue microstructure. Incorporation of more detailed physical models will facilitate understanding of the significant and application of this structure. With the recognition that this is not "diffusion diffraction" in the traditional sense, these intensity profile variations are nevertheless related to the pore geometry and so will be referred to as "diffraction-like" intensity patterns.

Figure 2:
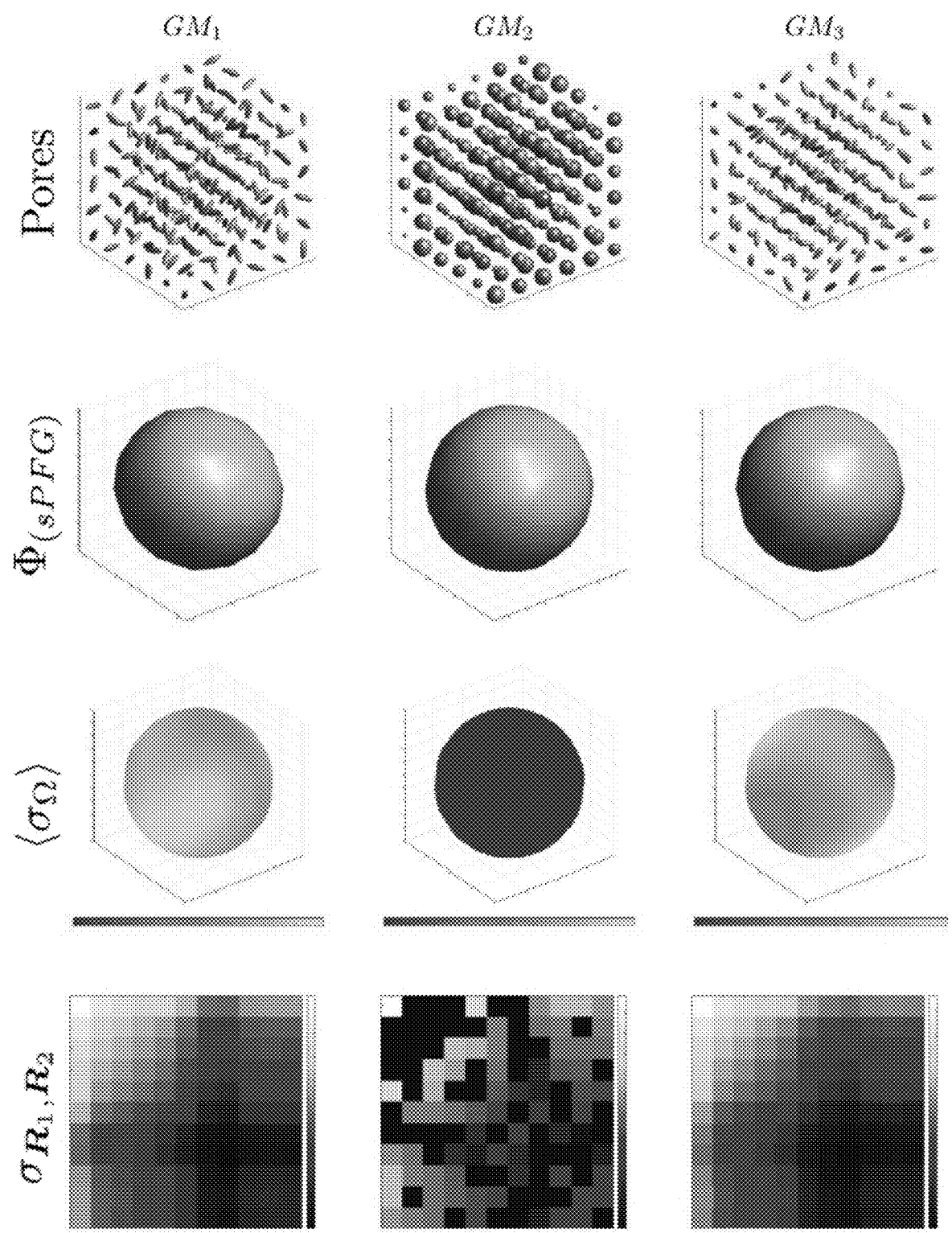
FIG. 2 illustrates a set of gray matter (GM) models with local diffusion profiles identical to the WM model in FIG. 1 but with random orientations ($GM_1$), all three eigenvalues the same at each pore (i.e., no anisotropy), but different between pores ($GM_2$), and random orientation and variable anisotropy ($GM_3$); the second row shows spin density function $\Phi$ estimated from a simulated sPFG acquisition which is approximately spherical; the third row shows DiTSI results of angular variance $\langle \sigma_{\Omega_1} \rangle$ of size (2L×2L) mapped onto a sphere where L=9 is the maximum spherical harmonic order; and the fourth row provides the DiTSI results of full radial variance $\sigma_{R_1,R_2}$.

FIG. 2 illustrates the GM tissue model simulation results. In the first model ($GM_1$), the local diffusion profiles are identical to the WM model but with random orientations. In the second model ($GM_2$), all three eigenvalues are the same in each pore (i.e., no anisotropy), but different between pores. The third model ($GM_3$) combines the first two, with random orientations and variations in the relative magnitude of the eigenvalues in each pore, but still ellipsoidal. The $\Phi$ estimated from an sPFG acquisition (Row 2) is approximately spherical, reflecting the fact that sPFG is sensitive only to macroscopic anisotropy, which these voxels do not possess, but not to their existing microscopic anisotropy. The angular variance $\langle \sigma_{\Omega_1} \rangle$ (Equation (15)) in Row 3 demonstrates the ability of DiTSI to detect the microscopic angular variations in both $GM_1$ and $GM_3$ with greater intensities representing directions of higher average microscopic anisotropy. In the case with no angular variation ($GM_2$), the angular variance is zero. In Row 4 are shown the DiTSI results of the full radial variance $\sigma_{R_1,R_2}$ (Equation 6). In both models that have ellipsoid diffusion profiles ($GM_1$ and $GM_3$), and hence a continuous (though bounded) range of radial dimensions, the results are similar to those FIG. 1, with a pronounced peak at the origin $R_1 = R_2$ and falloff consistent with the diffraction-like intensity profile variations related to the pore geometry. In $GM_2$, where only the radius is changed, only certain components consistent with the relatively few discretized radial variations are apparent. These results demonstrate the ability of DiTSI to detect both angular and radial variations in microscopic anisotropy.

Example 2: Application of DiTSI to Human dPFG Data

Acquisition and reconstruction parameters: To assess the translation of DiTSI into real human applications, we developed a modified version of the Extended Hybrid-space SENSE for EPI (EHSS-EPI,) pulse sequence able to collect sPFG and dPFG encoding in both the original dual spin echo (dPFG-DSE) and the single spin echo (dPFG-SSE) implementation. This method uses an off-resonance and eddy current corrected joint interleaved blip-up/down reconstruction and provides an efficient method for fast and accurate (i.e., distortion-free) acquisition, which will be critical for practical applications. Initial tests revealed that the dPFG-SSE version had significantly better signal-to-noise than the dPFG-DSE version and thus was the method used in the human studies. All data were collected on a General Electric (GE) Discovery MR750 3.0T Whole Body clinical imaging system using a 32-channel from NOVA Medical Devices (Wilmington, Mass.).

Figure 11:
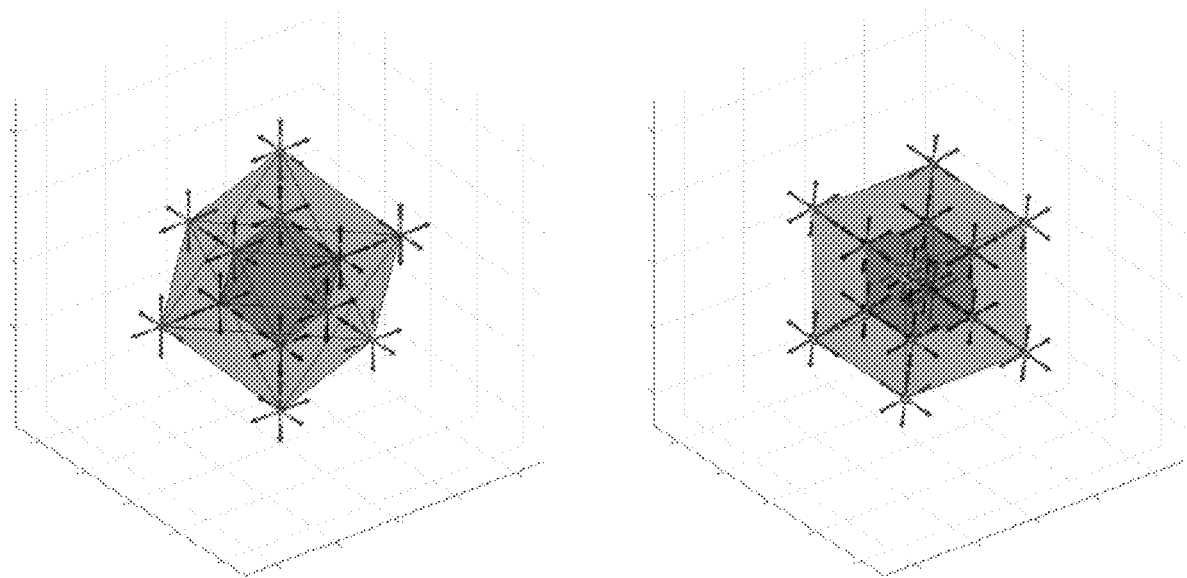
FIG. 11 shows the multi-shell octahedron (left) and cube (right) sampling used in the simulations and experimental data collection.

The dPFG sampling strategy used the cube sampling scheme shown in FIG. 11 (right). In this sampling scheme, there are eight non-orthogonal encoding directions. The reason for choosing this scheme is motivated below. The dPFG gradient pairs were defined by the Cartesian product at two different b-values: b=(1000, 2000) s/mm$^2$. The combinations of b-values and q-vectors were generated by the inner product of the two sets and produced 256 different diffusion encoded image volumes. An additional 2 image volumes without diffusion encoding (i.e., b=0) were also acquired. The EHSS-EPI sequence produced the entire set of 258 distortion-free images in 28 minutes. The acquisition parameters for the sPFG sequence were: slice thickness=2 mm, FOV=20 cm, TE=92.640 ms, TR=2.7 s, matrix size=100×100×72. The acquisition parameters for the dPFG sequence were slice thickness=2 mm, FOV=20 CM, TE=121.344 ms, TR=4.0 s, matrix size=100×100×72.

The reconstructions were run using the following parameters: angular discretization $l_{max}$=3, radial discretization $n_{max}$=6, spherical harmonics $L_{max}$=3, spherical Bessel $N_{max}$=6, grid size=13×13×13. The radial average was carried out for scales n=1 . . . 6 or from 0.18 to 1.1 mm (taking $\Delta$=50 ms, $\delta$=20 ms, $b_{max}$=2000 s/mm$^2$ and $R_n$=4$\pi^2$n$\sqrt{(\Delta-\delta/3)/b_{max}}$.

Figure 3:
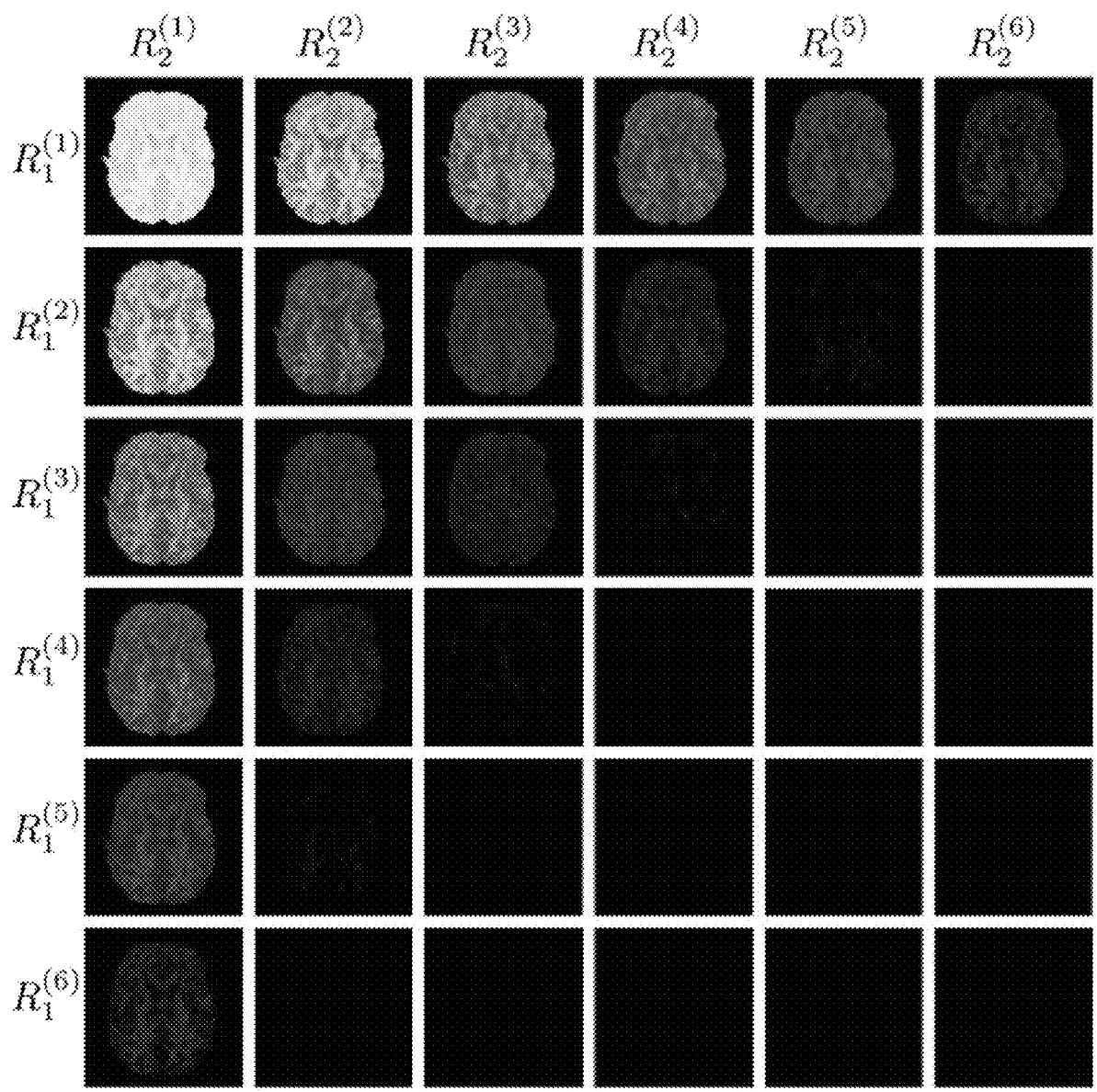
FIG. 3 shows the radial variance $\sigma_{R_1,R_2}$ for the human data computed for $(R_1, R_2)$ where $R_1 \in [1,6]$, $R_2 \in [1,6]$. The images are displayed on a log scale to better visualize the higher order channels.
Figure 4A:
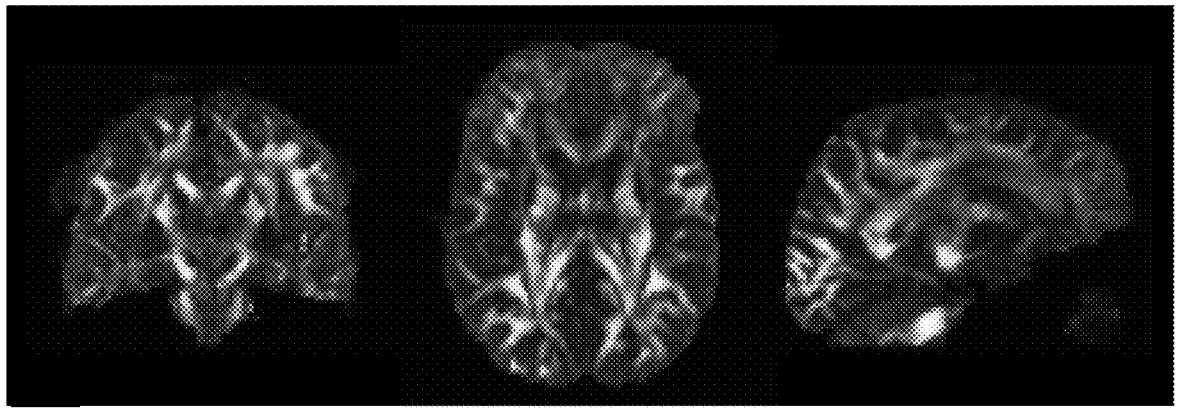
FIGS. 4A and 4B are parameter maps where
Figure 4B:
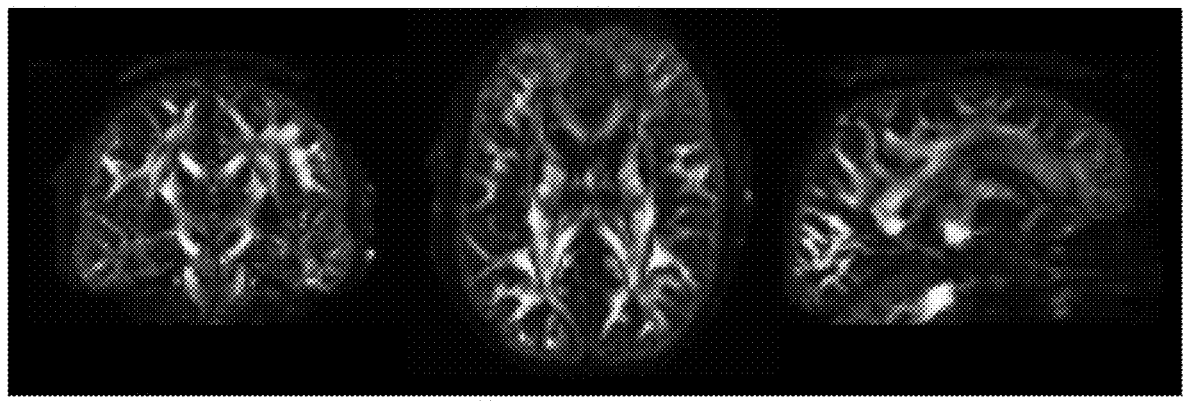
Figure 5:
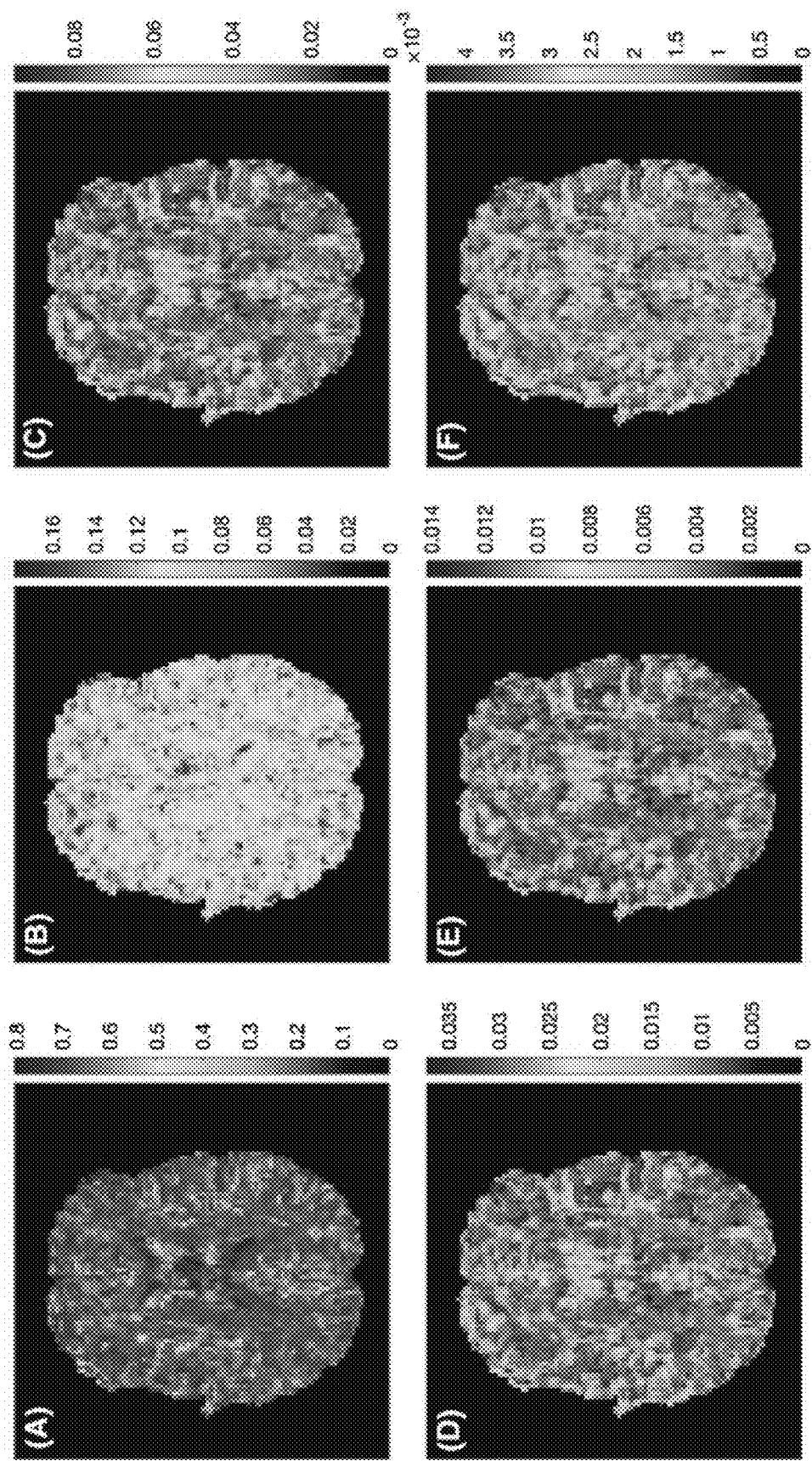
FIG. 5 illustrates the ratios of the first six components ((A)-(F)) of the radial standard deviation $\sigma_R^{ij}$, i=1, j=1, . . . , 6 (top row in FIG. 3) to the angular standard deviation $\sigma_\Omega$ in a normal human.

Results: The radial variance $\sigma_R$ on a normal human subject using HCP data collected at CFMRI is shown in FIG. 3. The real data acquisition includes the mixing time which was not included in the simulations. Therefore, the simulation results are symmetric relative to the order of pulses, i.e., $R_1$ and $R_2$ can be substituted for each other. The real data could possess some $R_1$, $R_2$ asymmetry as the order of pulses and not just their values becomes important. The first component of the radial standard deviation $\sigma_R(R_1^{(1)}, R_2^{(1)})$ is shown in FIG. 4A. The angular variance $\sigma_\Omega$ is shown in FIG. 4B. The ratio of the first six components of the radial standard deviation (top row in FIG. 3) to the annular standard deviation $\sigma^{ij}/\sigma_\Omega$ (FIG. 4B) in a normal human is shown in shown in FIG. 5. It is interesting to note that there appears to be an increase in spatial variations in lower right panel (F) of FIG. 5 consistent with the diffraction-like intensity profile variations observed in FIG. 1 and FIG. 2. As noted previously, but without intending to be bound by a particular theory, the source of this effect appears to be a result of the eigenstructure of the dPFG signal related to its limited range of the orientational anisotropy, and the fixed sampling/discretization size used for the data acquisition and analysis. Nonetheless, these results suggest a particular sensitivity of DiTSI to complex tissue microstructure.

Example 3: Application of JEDI to Human dPFG and sPFG Data

Acquisition and reconstruction parameters: To test the JEDI method, sPFG diffusion acquisition data was combined with the dPFG data acquired using the same EHSS-EPI pulse sequence (and reconstruction) described above. The protocol acquires 3 shells at b-values of b=(1000, 2000, 3000 s/mm$^2$ with the number of directions being 30, 45, and 60, respectively. The data acquisition parameters included slice thickness thk=2 mm, FOV=20 cm, TE=119 ms, TR=4.0 s, matrix size=100×100×72 with a SENSE factor of 4. The imaging time was 16 min. A standard high resolution anatomical (HRA) dataset was also collected using an inversion recovery prepared MP-RAGE protocol, 1.2 mm sagittal slices (S/I direction), Locs/slab=170, number of slabs=1, FOV=26 cm, TR/TE/FA=7 ms/3 ms/8°, Inversion time TI=900 ms, matrix size 256×256, BW=31.25 kHz, NEX=1.

Figure 6:
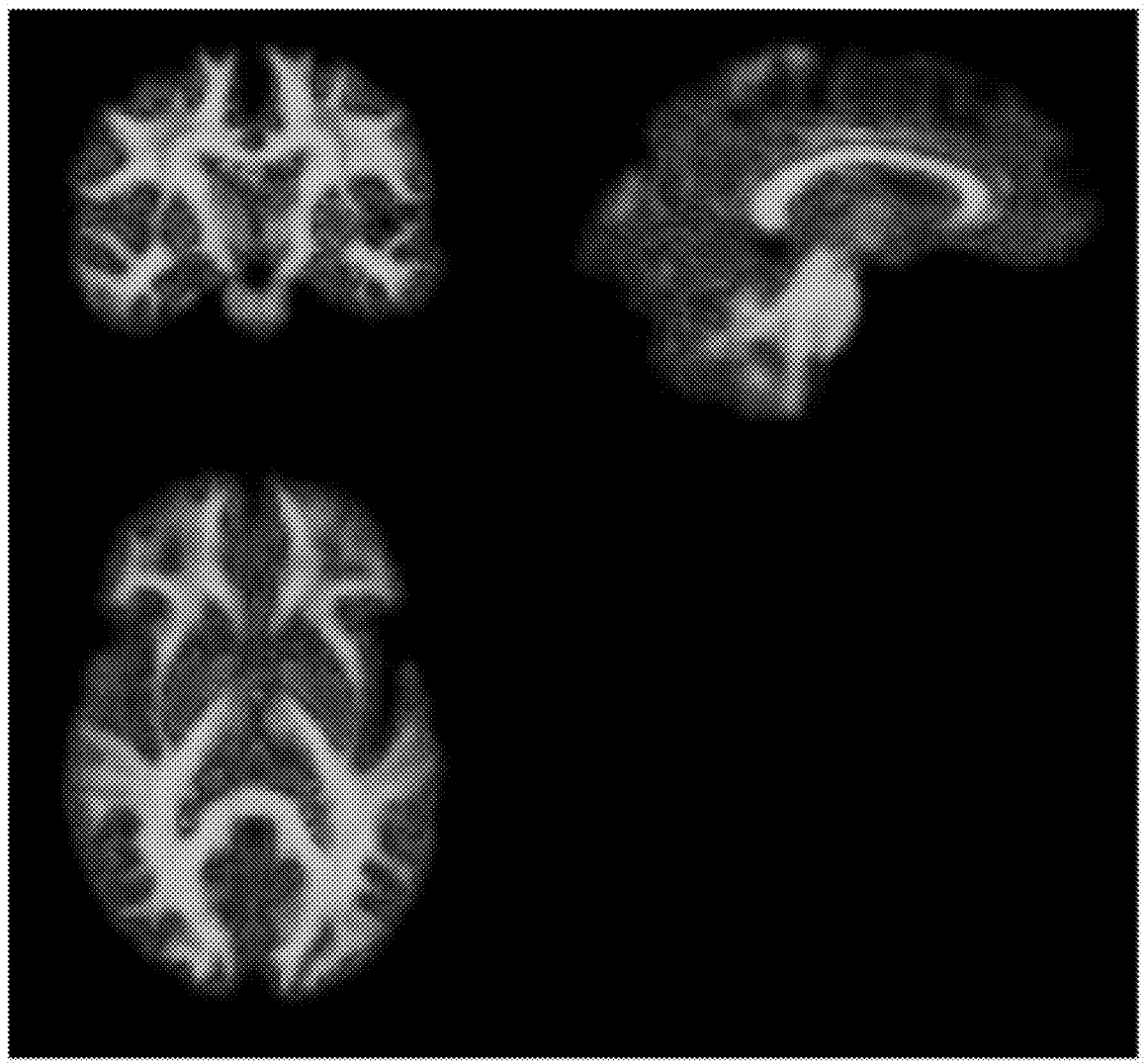
FIG. 6 illustrates three different views of a sample JEDI analysis according to the inventive method showing an overlay of the equilibrium probability fields generated by GO-ESP for sPFG (green) and joint sPFG+dPFG (red) acquisitions.
Figure 7:
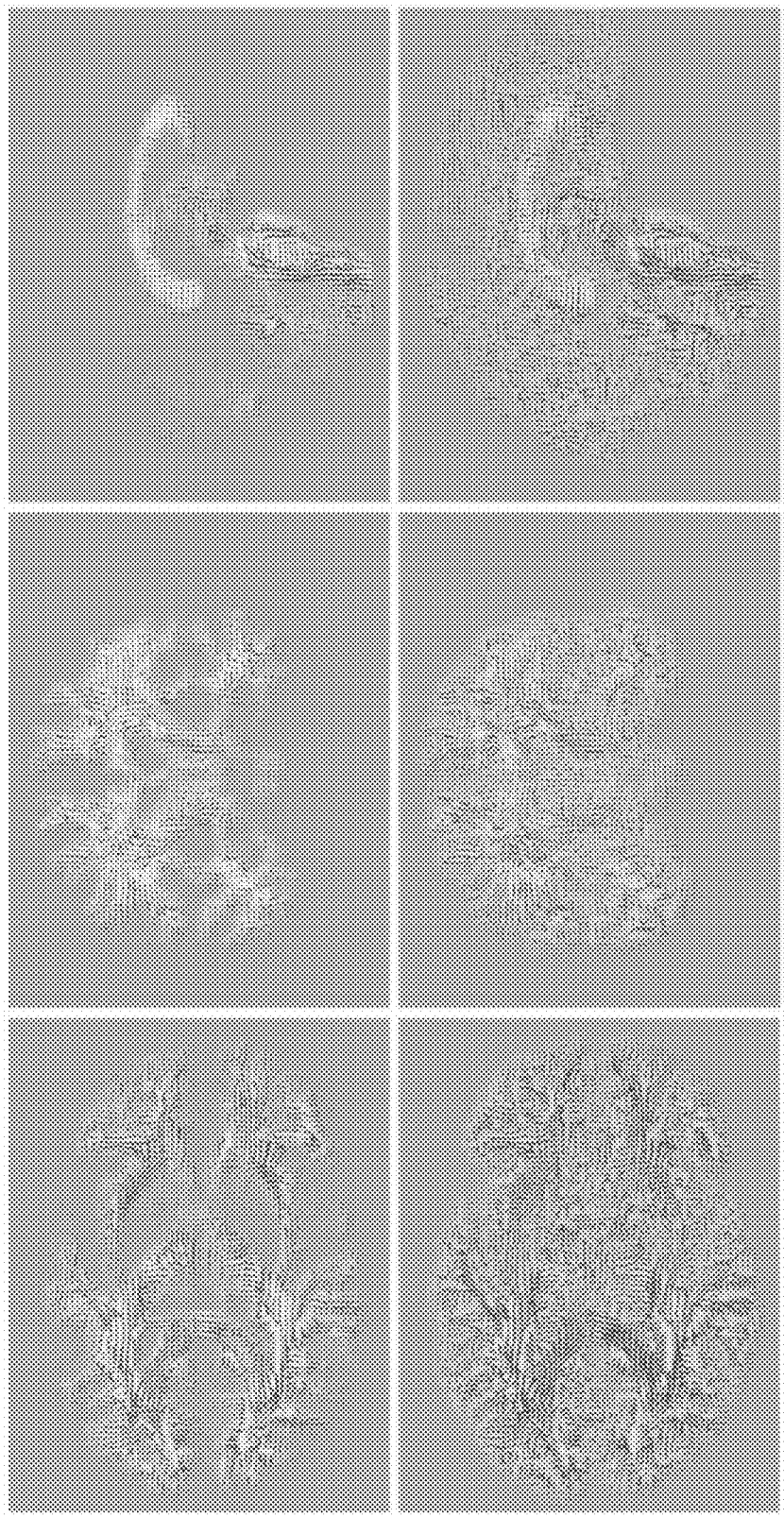
FIG. 7 provides an example of the results of JEDI analysis with a comparison of major eigenvector field for sPFG (top row) and joint sPFG+dPFG (bottom row) GO-ESP processing. The joint sPFG+dPFG processing clearly demonstrates continuous extension of the white matter fiber signatures to the gray matter areas.
Figure 12:
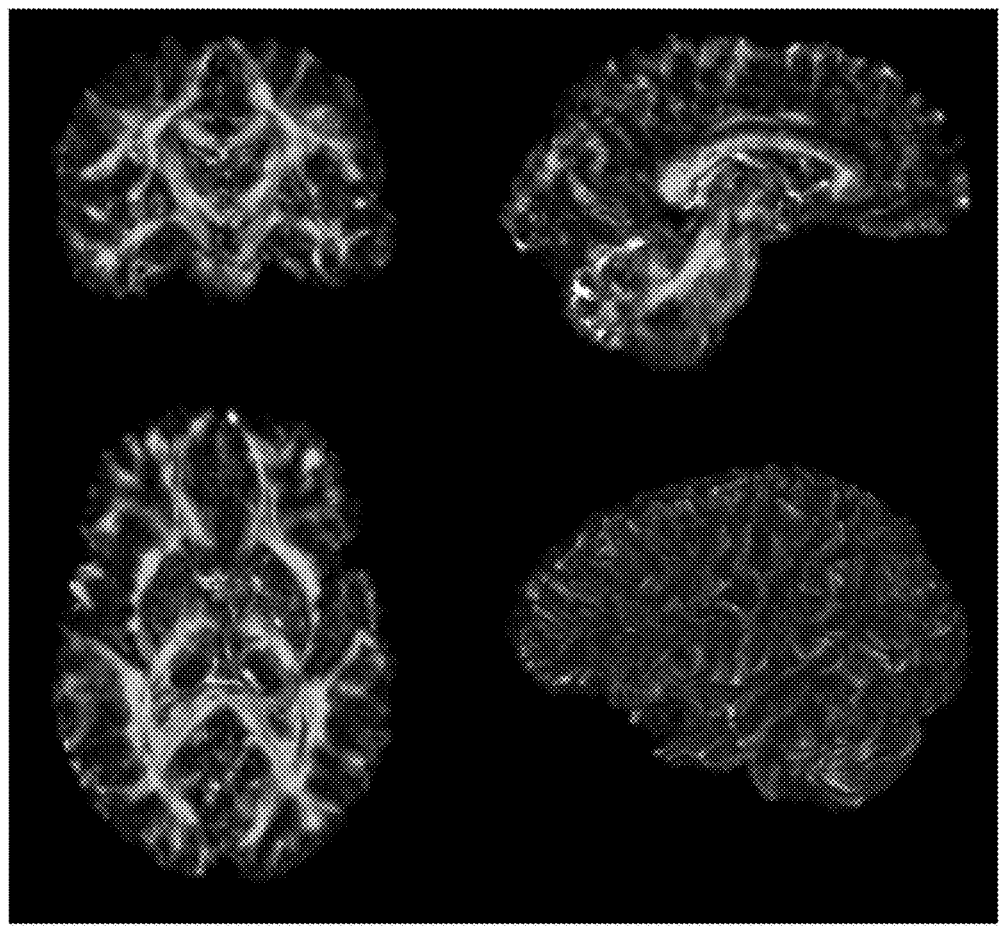
FIG. 12 illustrates the results of JEDI analysis according to the present invention, with an overlay of the major EMI mode amplitude produced by the GO-ESP full brain tractography (5M tracs total) by processing sPFG-only (green) and joint sPFG+dPFG (red) acquisitions. The joint sPFG+dPFG processing shows the extension of the connectivity modes into the gray matter regions.
Figure 13:
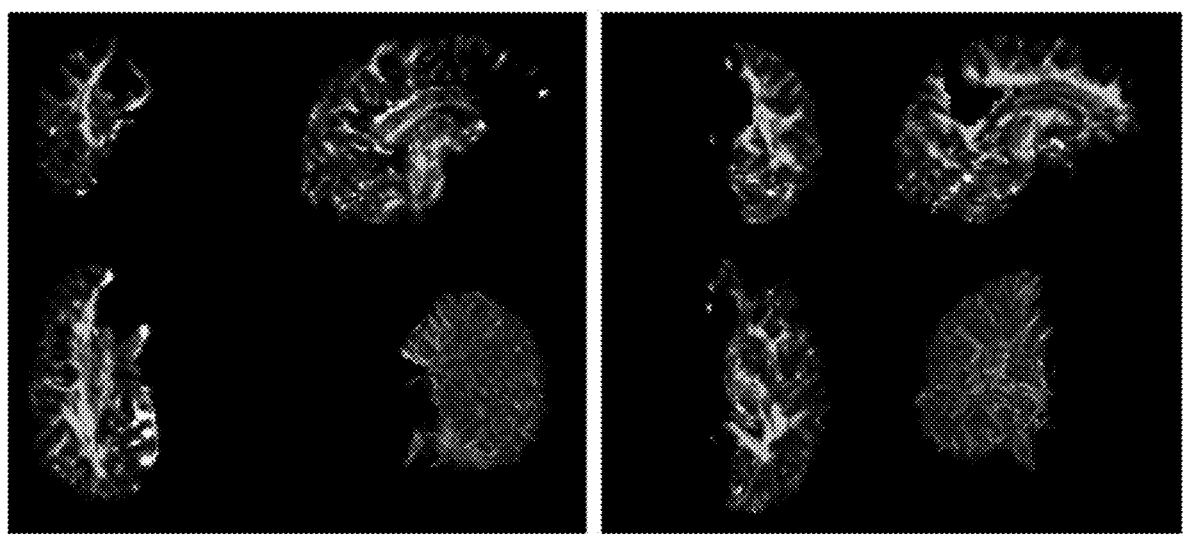
FIG. 13 illustrates overlay of amplitudes of the next 2 EMI modes produced by GO-ESP full brain tractography in addition to those shown in FIG. 12.

Results: The JEDI method, as an extension of the GO-ESP method, produces the same output: local anisotropy defined by the equilibrium probability (EP) is simultaneously estimated with the global fiber tracts (for details, see Galinsky and Frank, *IEEE Trans Med Imaging*, 2015; 34:1177-1193). A comparison of EP determined by GO-ESP using only the sPFG data (green) and by JEDI using both sPFG and dPFG data (red) is shown in FIG. 6 and clearly demonstrates that joint sPFG+dPFG processing using JEDI is capable of extending the EP white matter area detected by sPFG to the gray matter regions. This capability is also exhibited in a plot of the principal eigenvectors from sPFG (top row) and joint sPFG+dPFG (bottom row) processing shown in FIG. 7, which shows a continuous extension of the WM fiber signatures to the gray matter areas. An additional quantitative measure of connectivity are the eigenmodes of the connectivity matrix generated by GO-ESP tractography, which is referred to as "Eigenmode Imaging" ("EMI"). FIG. 12 shows an overlay of the major EMI mode amplitude produced by the GO-ESP full brain tractography (5M tracs total) by processing sPFG-only (green) and joint sPFG+dPFG (red) data. The joint sPFG+dPFG processing shows the extension of the connectivity modes into the gray matter regions. The amplitudes of the next two major eigenmodes are shown in FIG. 13.

Example 4: The "Gyral Bias" Problem

Figures 14A, 14B:
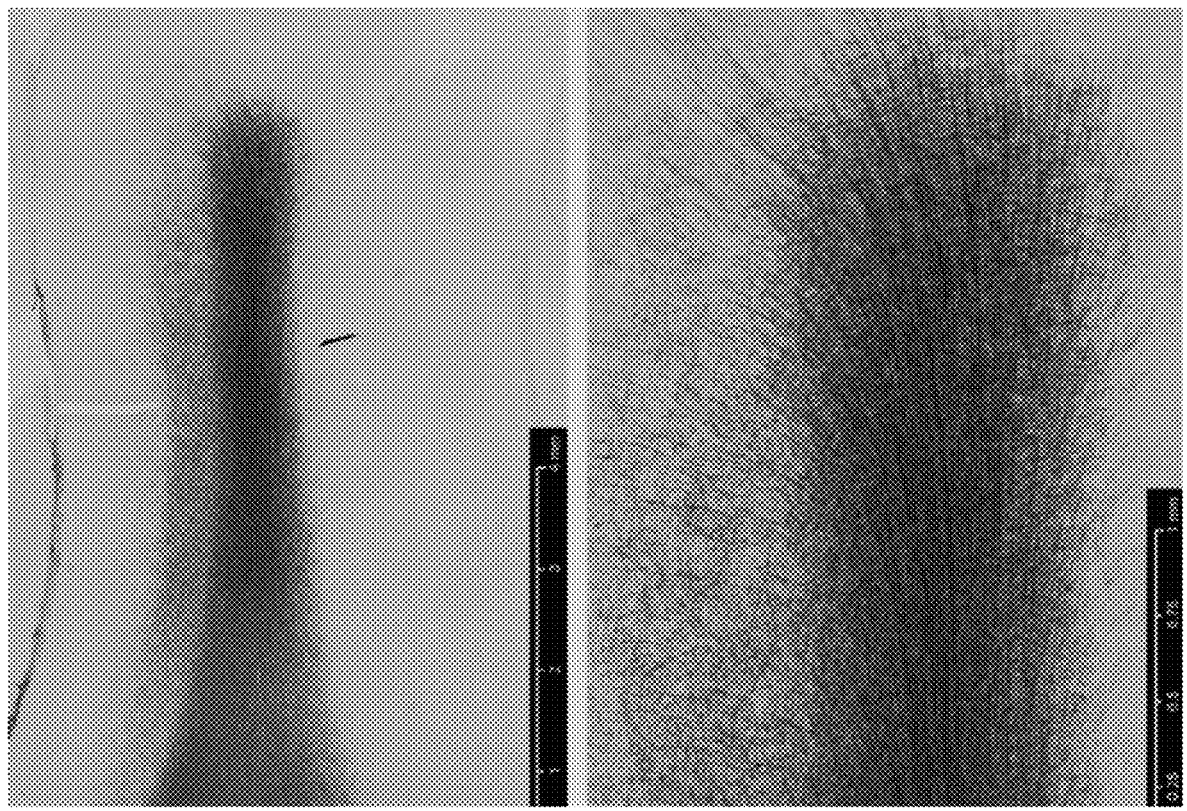
FIGS. 14A and 14B provide an illustrative example of the gyral bias problem using histological staining of myelinated axonal trajectories in a gyral blade of postnatal day 6 macaque brain.

A dramatic demonstration of the failure of standard sPFG methods to correctly discern local tissue microstructure in the presence of voxels with no (or limited) macroscopic anisotropy is evident in the so-called "gyral bias" problem. This exposes some important acquisition and analysis drawbacks plaguing current methods. The basic problem is as follows: A gyms is a ridge in the cerebral cortex, a fold whose curvature is positive with respect to the brain center. In a single "gyral blade" there is a thin finger of WM on the inside, covered by a layer of GM on the outside. WM fibers in these folded cortical regions eventually project into the GM regions, traversing the WM/GM boundary into the cortical layer. Because these tracts cross the WM/GM approximately perpendicular (i.e., normal) to this boundary, they have an interesting distribution of trajectories within any given gyms. Fiber projecting straight along the centroid of the gyms (referred to as the "gyral axis") all the way to the gyral crown passes through the WM/GM boundary at approximately 90°, to the boundary. However, fibers crossing below the crown must curve away from the gyral axis in order to cross perpendicular to the WM/GM border, resulting in highly curved fiber trajectories. A histological stain of the myelinated axons in a single gyral blade demonstrating these trajectories is shown in FIGS. 14A-14B.

Two obvious modes of failure for standard sPFG acquisition and analysis methods are thus evident. The first is related to the acquisition: sPFG methods are insensitive to voxels that exhibit no macroscopic anisotropy. This is basically the case in GM. Although some anisotropy may be evident in border voxels partially composed of WM, the overall the ability to characterize such voxels by the standard DTI model is compromised. Consequently, the diffusion anisotropy is "lost", i.e., goes undetected, in the GM and, at best, is degraded at these border regions. Thus, the detected WM pathways are those from voxels that are predominantly composed of WM—those along the gyral axis that are least influenced by both curvature and GM contamination. The fiber pathway most robustly reconstructed are those along the gyral axis that project into the gyral crown. This results in a reconstructed DTI principal vector map or in reconstructed fiber tracts biased towards straight fiber pathways projecting all the way to the gyral crown. Tractography streamlines tend to terminate primarily on gyral crowns, rather than the walls of sulci (or the sulcalfundi). This is the "gyral bias problem."

The gyral bias problem is not solely due to the presence of gray matter. It is also a consequence of the way tract reconstruction is usually performed. Standard tractography methods typically employ some relatively restrictive constraint on maximum fiber curvature (e.g. ≤45°) that is violated by the curvature of the fibers projecting into the GM along the gyral axis (up to 90°), save for those near the gyral crown. (It should be noted that these two are not unrelated, practically speaking, as the curvature of a single tract within a voxel, produces anisotropy in a range of directions along its path which can mimic a distribution of straight fiber orientations.) In voxels with multiple fiber orientations, many algorithms choose to propagate the track reconstruction along the path with the smallest angular deviation. The GO-ESP method does not need to make this choice as it is capable of tracking multiple fibers at arbitrarily large angles through a single voxel.

Figure 8:
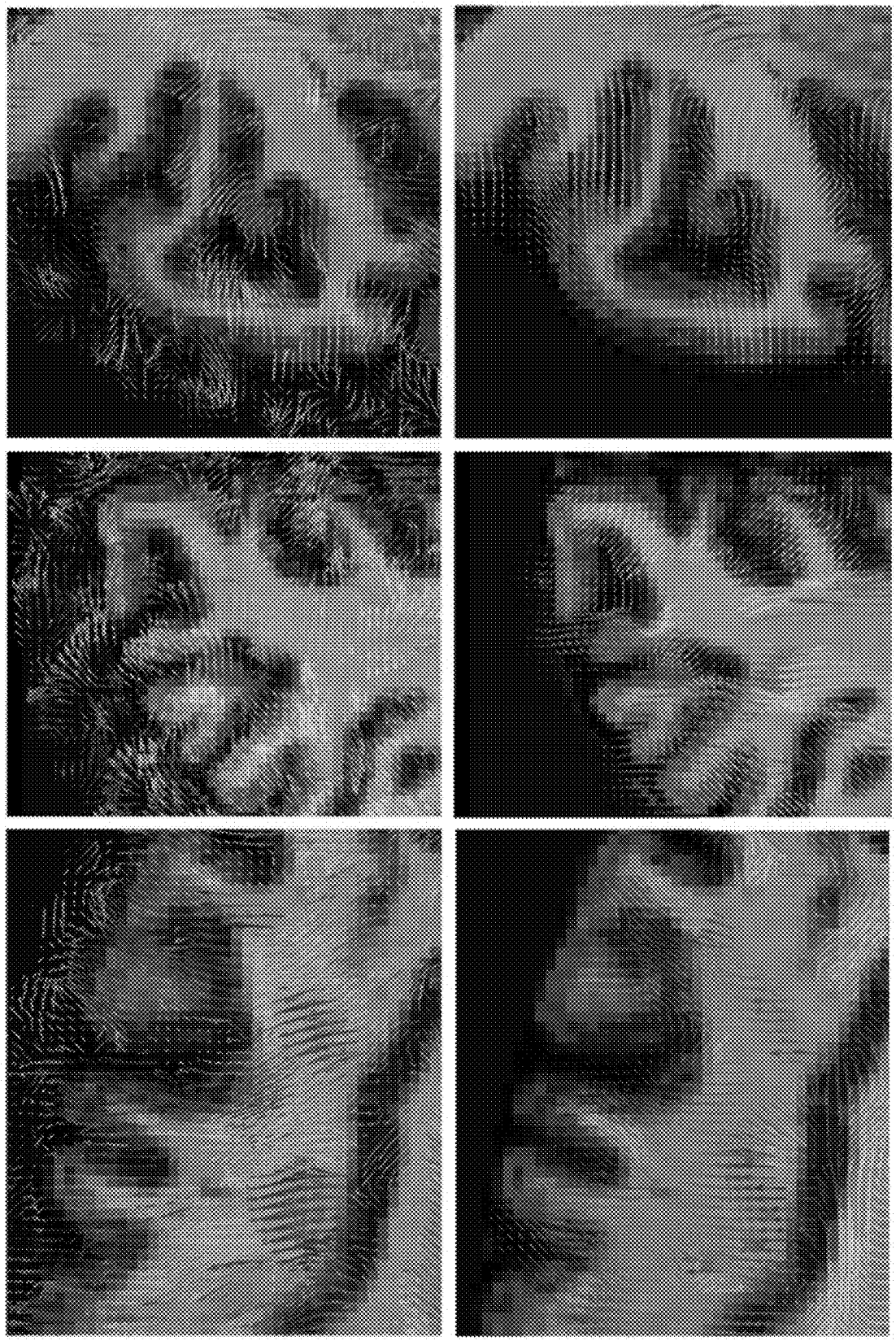
FIG. 8 illustrates an example of the gyral bias problem, comparing the principal eigenvectors generated by JEDI (bottom row) with those generating using FSL (top row), where the colors correspond to direction.
Figure 9:
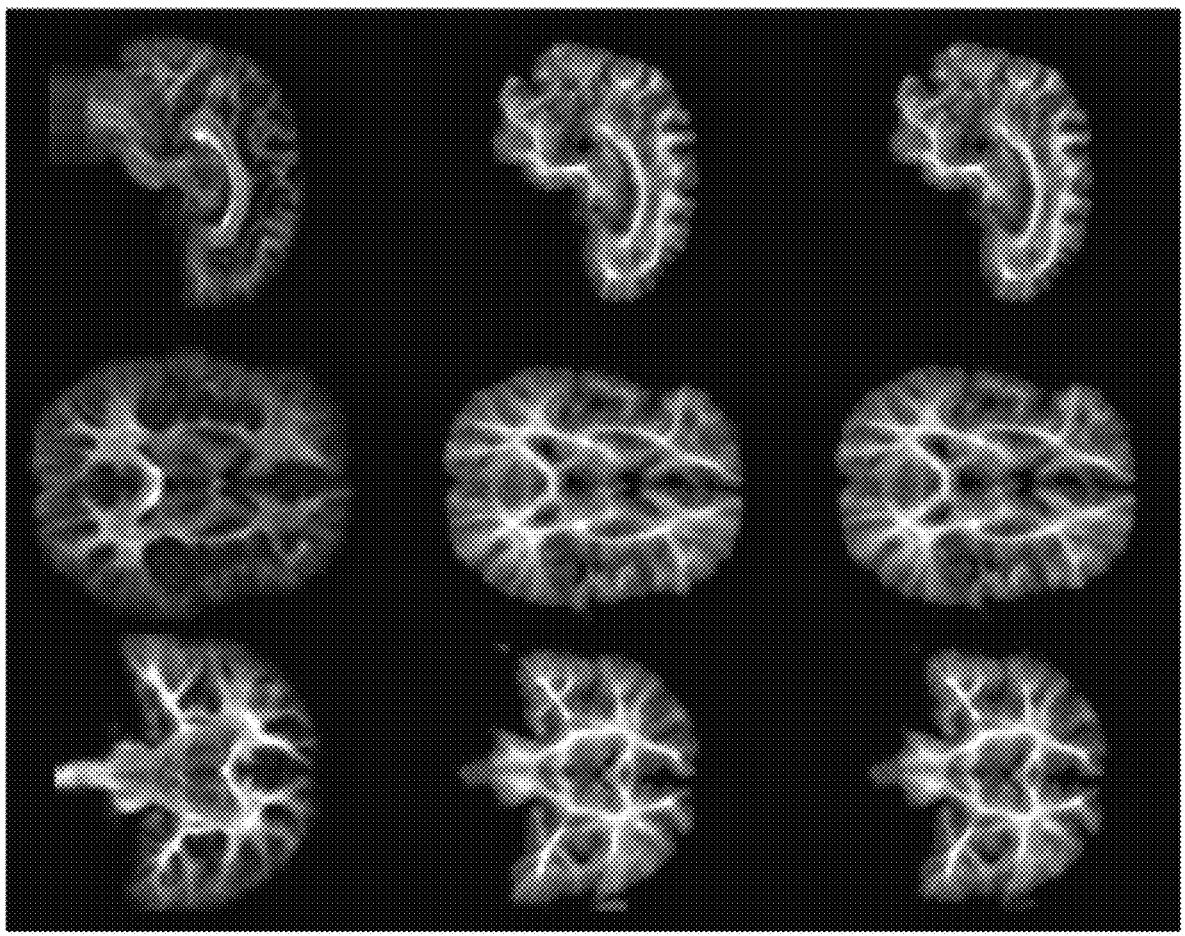
FIG. 9 illustrates another example of the gyral bias problem, comparing the results of JEDI analysis suing both sPFG and dPFG data (top row), GO-ESP using only sPFG data (middle row), and constrained spherical deconvolution (CSD) using MRtrix3 (as described by Schilling et al., *Human Brain Mapping*, 2018; 39:1449-1466).
Figure 10:
FIG. 10 illustrates the gyral bias problem, comparing the difference in fiber tract density computed from JEDI using both sPFG and dPFG data (FIG. 9, top row) and from using only sPFG data with GO-ESP (FIG. 9, middle row). The log of the positive differences is shown overlaid on the high-resolution anatomical data.

Some mitigation strategies for gyral bias have been suggested, but a robust solution must tackle both these problems simultaneously. The JEDI method is less susceptible to this bias for two reasons. First, the tracking method used is GO-ESP for which there is no limitation, i.e., upper bound, on the fiber curvature angle. This is a consequence of (as well as a primary motivation for) the geometric-optics approach it employs. Secondly, by incorporating dPFG data via DiTSI, it is capable of detecting microscopic anisotropy (including both radial and angular variations) in GM or voxels which contain a mixture of GM and WM. A demonstration of JEDI's mitigation or gyral bias effects is shown in FIGS. 8-10. FIG. 8 shows a comparison of the principal eigenvectors generated by JEDI with those generated using FSL in three brain regions near the cortical surface. The JEDI reconstructed vector fields show clear curved propagation from the gyral WM into the GM regions, whereas those generated by FSL do not. An additional measure of the gyral bias problem is the reduction of fiber tract density (computed from reconstructed fiber tracts) in GM regions. Overall, the smoothness and continuity of the JEDI vector field is significantly improved over the standard DTI analysis. For this example, we constructed two comparisons in order to illustrate the difference between the two failure modes discussed above. These two comparisons required three analysis methods.

We first compared just the sPFG data analyzed with constrained spherical deconvolution (using the MRtrix3 analysis package with $2.5 \times 10^6$ seed points) generated tract density images (sometimes referred to as "TDI"). This is shown in FIG. 9 (bottom row). Secondly, we analyzed this same dataset using GO-ESP to generate a density image FIG. 9 (middle row). Comparison of these two methods highlights the first issue concerning the limitations on the fiber curvature angle, which GO-ESP does not have. In addition, this highlights GO-ESP's ability to separate multiple fibers within a voxel with very small angular difference between them. It is worth re-emphasizing that GO-ESP is not performing any type of deconvolution but rather is taking advantage of prior information in the data through coupling of neighboring voxels via the theory of entropy spectrum pathways (ESP). Significant differences in the fiber density maps (reflecting differences in the tractography) are clearly evident between these two methods, particularly in regions of the most complex fibers crossing geometries, and in GM/WM border regions. Because GO-ESP exploits coupling with surround voxels, it is still able to detect small amounts of macroscopic anisotropy even in GM regions that exhibit even a small degree of macroscopic anisotropy, such as those near WM border regions where they are partial volumed with WM. Thirdly is JEDI analysis (FIG. 9, top row) where the dPFG analysis using DiTSI has been integrated with the sPFG data via JESTER and tracked using GO-ESP. The comparison with GO-ESP analysis shown in FIG. 9, middle row, thus highlights the additional information that is provided by the dPFG data. The GO-ESP algorithm using on sPFG data produces significantly more robust tract density images than CSD because of its ability to resolve multiple fibers crossing and the lack of a constraint on the fiber turning angle. The additional track density information detected by JEDI (joint sPFG+dPFG) over sPFG only (GO-ESP) is more subtle but still evident in color overlay in FIG. 10, where positive differences are overlayed in red, illustrating the additional fiber density information detected using JEDI. The log of the positive differences is shown overlaid on the high-resolution anatomical data. The increase in fiber tract density using JEDI is clearly evident in the gray matter and regions adjacent to it.

Generally speaking, the JEDI-generated tracks appear to be consistent with expected fiber pathways. It is also worth note that while the diffusion weighting in these data is large enough that no CSF signal is present, finite voxel size inevitably causes blurring of the cortical surface and sulcal region, and thus the potential for artifactual fiber densities in regions of CSF. However, the use of high-resolution anatomical data in the joint estimation should reduce this effect. These initial results demonstrate the potential for JEDI to mitigate the gyral bias problem, in addition to providing more robust and accurate whole-brain tractography results, which could have important implications for a wide range of research and clinical applications.

The utility of sPFG (i.e., standard DTI) methods in the assessment of local tissue properties and global connectivity has been demonstrated in a variety of applications, however, it is also recognized as an approximate method predicated on a highly organized intravoxel fiber structured dominated by fibers all pointing in the same direction, and thus with an average macroscopic, i.e., voxel, PDF that represented the microscopic (sub-voxel) PDF's loosely associated with single fibers. In reality, voxel dimensions ($\approx 2$ mm$^3$) are orders of magnitude larger than fiber dimensions and the human brain has a very complex organization of WM fiber pathways, together which conspire to virtually guarantee the failure of the standard DTI model of a "single fiber".

As the recognition of the effect of the intravoxel tissue complexity became apparent, a host of more advanced methods based on higher order tensor models were proposed. Eventually it was recognized that the complexity of intravoxel diffusion profiles does not lend itself well to any analytical model, which led to the development of more general nonparametric (model-free) approaches where the goal is to measure the displacement probability density function or diffusion propagator directly and the natural extension of this to imaging wherein 3D Cartesian sampling of q-space is used to obtain the 3D displacement probability density function (dPDF) at each voxel. This recognition has recently spawned more practical methods for obtaining an estimate of the dPDF, often called the ensemble average propagator (EAP), from more practical multi-shell, multi-directional acquisitions, aided by recent advances in parallel imaging that allow the acquisition of significantly more diffusion encoding directions per unit time and multiple shells (i.e., multiple b-values) of data.

However, the continued emphasis on the intravoxel dPDF was ultimately a limited strategy because it ignores information from neighboring regions. Further, it leads to a logical inconsistency implicit in subsequent tractography: one first estimates the intravoxel PDF, then constructs tracts from these across voxels. The first presumes independence of the voxels, the second implies dependence. Both cannot simultaneously be true. In reality, the fact that human tissues tend to be organized over spatial scales far greater than voxel dimensions implies that diffusion measurements should also be highly correlated over multiple voxels and thus from a purely formal perspective provides highly relevant prior information about both the local and long-range structures estimated from intravoxel diffusion measurements. We formalized this notion be constructing a probabilistic (Bayesian) formulation in which the local (PDF) and surrounding (coupling) information were incorporated using the theory of entropy spectrum pathways (ESP), implemented within a geometric optics scheme called GO-ESP for mapping trajectories of high probability. In this theory, the transition probability between voxels, rather than the PDF, emerges as the critical quantity of interest from which both the local anisotropy (via the "equilibrium probability", or EP) and the global tractography are derived. This method was shown to be capable of estimating multiple fibers crossings within a voxel with down to 8° angular resolution and was subsequently used to demonstrate that the global structure of white matter fibers in the human brain are well described by a lamellar vector field.

Ultimately, sPFG data is limited by the mismatch between the spatial resolution of the acquisition and the dimensions of the diffusion confining structure within the voxels (cells, fibers, etc.). The recognition of this fact led to the resurrection of using multiple wave-vector diffusion encoding schemes, typically in the form of dPFG, to probe voxels that possess microscopic anisotropy yet demonstrate a macroscopically isotropic diffusion profile. Theoretical work elucidated the dPFG signal characteristics in a variety of analytically well-defined architectures and diffusion distribution regimes and the quantity compartment shape anisotropy, or "CSA", emerged as the preferred metric for microscopic anisotropy. This led to a currently popular scalar measure—the so-called "fractional compartment eccentricity", or "FE", which is a dPFG analogue of the fractional anisotropy (FA) used in sPFG. Like the FA, the FE provides a simple, easy to calculate quantity that reflects some aspects of the local diffusion profile. But like FA, the FE is also too simple a measure to adequately unravel the influence of the tissue microstructure and physiology on the acquired signal. The situation is thus not dissimilar to the analysis problem presented by sPFG.

However, reliance on analytical models is ultimately an unrealistic characterization of fiber architecture and thus poses the threat of implicitly constraining the derived quantities to unrealistic estimates of the fiber architecture. The Diffusion Tensor Subspace Imaging, or "DiTSI", approach described herein for dPFG data is similar in spirit (and practice) to the EAP approach for sPFG data where we abandon the hope of a model and instead reconstruct the spin density function function $\Phi(r, R_1, R_2)$ directly. The additional novel feature of this approach is that this high dimensional spin density derived from dPFG data possesses highly informative subspaces that can be determined computationally as the projections of the higher dimensional space of the full spin density function. These subspaces exist in both the radial and the angular dimensions, and thus facilitate the extraction of information at multiple radial and angular scales. Simpler scalar metrics for spatial and angular anisotropy can be constructed by integration of these different subspaces. The access to information at a voxel subscale provided by the DiTSI characterization of the dPFG data provides a natural complement to the more macroscopic information provided by sPFG data analyzed by the GO-ESP method. These two sources of information can be integrated into a single processing scheme (JEDI) through the JESTER method that combines both microscopic and macroscopic diffusion information and thus produces more accurate estimates of both local anisotropy (as expressed by the EP) and global structural connectivity (expressed as tract eigenmodes derived from tractography).

In the first test of the JEDI concept, we collected data using a standard dPFG gradient scheme constructed from the Cartesian product of the vertices of the platonic solid icosahedron (FIG. 11, left). These vertices are orthogonal and thus their Cartesian products are either parallel or perpendicular. Therefore, directional information derived from the microscopic measurements is constrained to orthogonal sheet-like structures, which were clearly evident in our first JEDI tractography results. This recognition of the contribution of the DiTSI component of the JEDI scheme to the tracking clearly motivated the need for higher angular resolution dPFG data, leading to use of the scheme generated from the 8 vertices of a cube (FIG. 11, right) is shown the results using the same sPFG sampling scheme but a dPFG. These vectors are non-orthogonal (and there are more of them) and are able to better discriminate sub-voxel angular dependencies, which gets translated via JEDI into more detailed and accurate tractography, at the clear cost of time—the addition of 2 addition vectors increases the number of scans to 256 and lengthens the scan time to almost 28 min. The Cartesian product scheme quickly translates this into a large number of measurements and a prohibitively long scan times. In lieu of faster scanners, clearly more efficient sampling strategies are necessary.

It should be noted that in the Cartesian product scheme employed herein there are gradient pairs that are parallel. These are identical to sPFG diffusion sensitization along one particular direction, which suggests the possibility that a single pulse sequence with dPFG encodings carefully selected might be able to simultaneously collect both dPFG and sPFG data for input into the JEDI processing scheme, and thus provide a method that can truly be used for whole brain dMRI, being sensitive to both GM and WM.

The initial demonstration of the mitigation of the gyral bias problem has potentially important clinical significance in disorders such as Traumatic Brain Injury (TBI) where GM/WM interfaces have been hypothesized to be preferentially impacted.

In summary, the methods of analysis that provide advantages over existing methods for analyzing both sPFG and dPFG data. The diffusion tensor subspace imaging (DiTSI) method is a novel approach to analyzing dPFG data, extracting information over a range of angular and spatial scales. This information can be combined with sPFG data into our GO-ESP method for enhanced estimates of both local anisotropy and global tractography using the novel joint estimation diffusion imaging (JEDI).

REFERENCES (INCORPORATED HEREIN BY REFERENCE)

1. Frank L R, Galinsky V L. Information pathways in a disordered lattice. *Phys Rev E*. 2014; 89:032142-032152,
2. Galinsky V L, Frank L R. Simultaneous multi-scale diffusion estimation and tractography guided by entropy spectrum pathways, *IEEE Trans Med Imaging*. 2015; 34:1177-1193.
3. Galinsky V L, Frank L R. A unified theory of neuro-MRI data shows scale-free nature of connectivity modes. *Neural Comput.* 2017; 29:1441-1467.
4. Galinsky V I, Frank L R. The lamellar structure of the brain fiber pathways. *Neural Comput.* 2016; 28:2533-2556,
5. Cheng Y, Cory D G. Multiple scattering by NMR. *J Am Chem Soc.* 1999; 121:7935-7936.
6. Komlosh M E, Horkay F, Freidlin R Z, Nevo U, Assaf Y, Basser P J. Detection of microscopic anisotropy in gray matter and in a novel tissue phantom using double Pulsed Gradient Spin Echo M R. *J Magn Reson.* 2007; 189:38-45.
7. Özarslan E, Shemesh. N, Basser P. A general framework to quantify the effect of restricted diffusion on the NMR signal with applications to double pulsed field gradient NMR experiments. *J Chem Phys.* 2009; 130:104702.
8. Komlosh M E, Lizak M J, Horkay F, Freidlin R Z, Basser P J. Observation of microscopic diffusion anisotropy in the spinal cord using double-pulsed gradient spin echo MRI. *Magn Reson Med.* 2008; 59:803-809.
9. Lawrenz M, Finsterbusch J. Detection of microscopic diffusion anisotropy on a whole-body M R system with double wave vector imaging. *Magn Reson Med* 2011; 66:1405-1415.
10. Shemesh N, Ozarslan E, Basser P J, Cohen Y. Accurate noninvasive measurement of cell size and compartment shape anisotropy in yeast cells using double-pulsed field gradient M R. *NMR Biomed.* 2012; 25:236-246.
11. Cory D G, Garroway A N, Miller J R Applications of spin transport as a probe of local geometry. *Polym Preprints.* 1990; 31:149-150.
12. Mitra P. Multiple wave-vector extensions of the NMR pulsed-field-gradient spin-echo diffusion measurement. *Phys Rev B.* 1995; 51:15074-15078.
13. Özarslan E, Basser P J. M R diffusion-"diffraction" phenome-non in multi-pulse-field-gradient experiments. *J Magn Reson.* 2007; 188:285-294.
14. Lawrenz M, Koch M A, Finsterbusch J. A tensor model and measures of microscopic anisotropy for double-wave-vector diffusion-weighting experiments with long mixing times. *J Magn Reson.* 2010; 202:43-56.
15. Komlosh M E, Özarslan E, Lizak M J, Pore diameter mapping using double pulsed-field gradient MRI and its validation using a novel glass capillary array phantom. *J Magn Reson.* 2011; 208:128-135.
16. Özarslan E, Nevo U, Basser P J. Anisotropy induced by macroscopic boundaries: surface-normal mapping using diffusion-weighted imaging. *Biophys J.* 2008; 94:2809-2818.
17. Finsterbusch J, Koch M A, A tensor approach to double wave vector diffusion weighting experiments on restricted diffusion. *J Magn Reson.* 2008; 195:23-32.
18. Koch M A, Finsterbusch J. Compartment size estimation with double wave vector diffusion weighted imaging. *Magn Reson Med.* 2008; 60:90-101.
19. Jespersen S N. Equivalence of double and single wave vector diffusion contrast at low diffusion weighting. *NMR Biomed.* 2011; 25:813-818.
20. Benjamini D, Katz Y, Nevo U. A proposed 2D framework for estimation of pore size distribution by double pulsed field gradient NMR. *J Chem Phys.* 2012; 137:224201.
21. Benjamini D, Nevo U. Estimation of pore size distribution using concentric double pulsed-field gradient NMR. *J Magn Reson.* 2013; 230:198-204.
22. Benjamini D, Elsner J J, Zilberman M, Nevo U. Pore size distribution of bioresorbable films using a 3-D diffusion NMR method. *Acta Biomater.* 2014; 10:2762-2768.
23. Benjamini D, Komlosh M E, Basser P J, Nevo U. Nonparametric pore size distribution using dPFG: Comparison to s-PFG and migration to MRI. *J Magn Reson.* 2014; 246:36-45.
24, Benjamini D, Komlosh M E, Holtzclaw L A, Nevo U, Basser P I White matter microstructure from nonparametric axon diameter distribution mapping. *NeuroImage.* 2016; 135:333-344.
25. Özarslan E. Compartment shape anisotropy (CSA) revealed by double pulsed field gradient M R. *J Magn Reson.* 2009; 199:56-67.
26. Shemesh N, Westin C F, Cohen Y. Magnetic resonance imaging by synergistic diffusion-diffraction patterns. *Phys Rev Lett.* 2012; 108:058103.
27. Lawrenz M, Finsterbusch J. Double-wave-vector diffusion-weighted imaging reveals microscopic diffusion anisotropy in the living human brain. *Magn Reson Med.* 2013; 69:1072-1082,
28. Avram A V, Özarslan E, Sarlls J E, Basser P J. In vivo detection of microscopic anisotropy using quadruple pulsed-field gradient (qPFG) diffusion MRI on a clinical scanner. *NeuroImage.* 2013; 64:229-239.
29. Lawrenz N I, Finsterbusch J. Double-wave-vector diffusion-weighting experiments with multiple concatenations at long mixing times. *J Magn Reson.* 2010; 206:112-119.
30. Koch M A, Finsterbusch J. Towards compartment size estimation in vivo based on double wave vector diffusion weighting. *NMR Biomed.* 2011; 24:1422-1432.
31. Komlosh M E, Özarslan E, Lizak M J. Mapping average axon diameters in porcine spinal cord white matter and rat corpus callosum using d-PFG NeuroImage. 2013; 78:210-216.
32. Jespersen S N, Lundell H, SØnderby C K, Dyrby T B. Orientationally invariant metrics of apparent compart- 32. ment eccentricity from double pulsed field gradient diffusion experiments. *NMR Biomed.* 2013; 26:1647-1662.
33. Schilling K, Gao Y, Janve V, Stepniewska I, Landman B A, Anderson A W. Confirmation of a gyral bias in diffusion Mill fiber tractography. *Human Brain Mapping.* 2018; 39:1449-1466.
34. Jaynes E T. *Probability Theory: The Logic of Science.* New York, N.Y.: Cambridge University Press; 2003.
35. Burda Z, Duda J, Luck J M, Waclaw B. Localization of the maximal entropy random walk. *Phys Rev Lett.* 2009; 102:160602.
36. Jaynes E T. *Probability Theory with Applications in Science and Engineering.* Dallas, Tex.: Saucony Oil Company; 1958.
37. Jaynes E T. Macroscopic prediction. In: Haken H, ed. *Complex Systems—Operational Approaches in Neurobiology, Physics, and Computers.* Berlin: Springer-Verlag; 1985. p. 254-269.
38. Galinsky V L, Frank L R. A unified theory of neuro-MRI data shows scale-free nature of connectivity modes. *Neural Comput.* 2017; 29:1441-1467.
39. Novikov D S, Fieremans E, Jespersen S N, Kiselev V G. Quantifying brain microstructure with diffusion M M: Theory and parameter estimation. *NMR Biomed.* 2018; 43:e3998.
40. Grabert H, Green M. Fluctuations and nonlinear irreversible processes. *Phys Rev A.* 1979; 19:1747-1756.
41. Galinsky V L, Frank L R. The lamellar structure of the brain fiber pathways. *Neural Comput.* 2016; 28:2533-2556.
42. Reisert M, Kiselev V G, Dihtal B, Keliner E, Novikov D S. MesoFT: unifying diffusion modelling and fiber tracking. *Med Image Comput Comput Assist Interv.* 2014; 17:201-208.
43. Enßlin T A, Frommert M, Kitaura F S. Information field theory for cosmological perturbation reconstruction and nonlinear signal analysis. *Phys Rev D.* 2009; 80:105005.
44. Frank L R, Galinsky V L. Detecting spatio-temporal modes in multivariate data by entropy field decomposition. *J Phys A.* 2016; 49:395001.
45. Frank L R, Galinsky V L. Dynamic multi-scale modes of resting state brain activity detected by entropy field decomposition. *Neural Comput.* 2016; 28:1769-1811.
46. Frank L R, Galinsky V L, Orf L, Wurman J M. Dynamic multiscale modes of severe storm structure detected in mobile Doppler radar data by entropy field decomposition. *J Atmos Sci.* 2018; 75:709-730.
47. Galinsky V L, Frank L R. Automated segmentation and shape characterization of volumetric data. *Neuroimage.* 2014; 92:156-168.
48. Galinsky V L, Martinez A, Paulus M P, Frank L R. Joint estimation of effective brainWave activation modes using EEG/MEG sensor arrays and multimodal M M volumes. *Neural Comput.* 2018; 30:1725-1749.
49. Frank L R, Galinsky V L. Dynamic multi-scale modes of resting state brain activity detected by entropy field decomposition. *Neural Comput.* 2016; 28:1769-1811.
50. Novikov D S, Kiselev V G, Jespersen S N. On modeling. *Magn Reson Med.* 2018; 79:3172-3193.
51. Dale A M, Fischl B, Sereno M I. Cortical surface-based analysis. I. Segmentation and surface reconstruction. *Neuroimage.* 1999; 9:179-194.
52. Yopak K E, Berquist R M, Galinsky V L, Frank L R. Quantitative classification of cerebellar foliation in cartilaginous fishes (Class: Chondrichthyes) using 3D shape analysis and its implications for evolutionary biology. *Brain Behavior Evolution.* 2016; 87:252-264.
53. Galinsky V L, Frank L R. Symplectomorphic registration with phase space regularization by entropy spectrum pathways. *Magn Reson Med.* 2019; 81:1335-1352.
54. Frank L R, Galinsky V L, Orf L, Wurman J M. Dynamic multiscale modes of severe storm structure detected in mobile Doppler radar data by entropy field decomposition. *J Atmos Sci.* 2018; 75:709-730.
55. Galinsky V L, Martinez A, Paulus M P, Frank L R. Joint estimation of effective brainWave activation modes using EEG/MEG sensor arrays and multimodal MRI volumes. *Neural Comput.* 2018; 30:1725-1749.
56. Callaghan P T. *Principles of Nuclear Magnetic Resonance Microscopy.* Oxford: Oxford Science Publications; 1991.
57. Yeh F C, Wedeen V J, Tseng W Y. Generalized q-sampling imaging. *IEEE Trans Med Imaging.* 2010; 29:1626-1635.
58. Frank L R, Galinsky V L. Detecting spatio-temporal modes in multivariate data by entropy field decomposition. *J Phys A.* 2016; 49:395001.
59. Galinsky V L, Frank L R. Simultaneous multi-scale diffusion estimation and tractography guided by entropy spectrum pathways. *IEEE Trans Med Imaging.* 2015; 34:1177-1193.
60. Zahneisen B, Aksoy M, Maclaren J, Wuerslin C, Bammer R. Extended hybrid-space SENSE for EPI: off-resonance and eddy current corrected joint interleaved blip-up/down reconstruction. *NeuroImage.* 2017; 153:97-108.
61. Van Essen D C, Smith S M, Barch D M, The WU-Minn human connectome project: an overview. *NeuroImage.* 2013; 80:62-79.
62. Reveley C, Seth A K, Pierpaoli C, Superficial white matter fiber systems impede detection of long-range cortical connections in diffusion M R tractography. *PNAS.* 2015; 112:E2820-E2828.
63. Reveley C. Local Structure and Global Connectivity in The Cerebral Cortex. PhD thesis, University of Sussex; 2017.
64. Van Essen D C, Jbabdi S, Sotiropoulos S N, et al. Chapter 16—*Mapping Connections in Humans and Non-Human Primates: Aspirations and Challenges for Diffusion Imaging.* Second ed. London, U K; Waltham, Mass.: Elsevier; 2013.
65. St-Onge E, Daducci A, Girard G, Descoteaux M. Surface-enhanced tractography (SET). *NeuroImage.* 2018; 169:524-539.
66. Smith S M, Jenkinson M, Woolrich M W, Advances in functional and structural M R image analysis and implementation as FSL. *NeuroImage.* 2004; 23:S208-S219.
67. Jenkinson M, Beckmann C F, Behrens T E, Woolrich M W, Smith S M. FSL. *Neuroimage.* 2012; 62:782-790.
68. MRTrix3: advanced tools for the analysis of diffusion MRI data; 2019. on the world wide web at mrtrix.org
69. Calamante F, Tournier J D, Jackson G D, Connelly A. Track-density imaging (TDI): super-resolution white matter imaging using whole-brain track-density mapping. *NeuroImage.* 2010; 53:1233-1243.
70. Grebenkov D S. NMR survey of reflected Brownian motion. *Rev Mod Phys.* 2007; 79:1077-1137.
71. Frank L R. Anisotropy in high angular resolution diffusion weighted M M. *Magn Reson Med.* 2001; 45; 935-939.
72. Tuch D S, Reese T G, Wiegell M R, Makris N, Belliveau J W, Wedeen V J. High angular resolution diffusion imaging reveals intravoxel white matter fiber heterogeneity. *Magn Reson Med.* 2002; 48:577-582.

73. Frank L R. Characterization of anisotropy in high angular resolution diffusion weighted MRI. *Magn Reson Med.* 2002; 47:1083-1099.
74. Özarslan E, Mareci T H. Generalized diffusion tensor imaging and analytical relationships between diffusion tensor imaging and high angular resolution diffusion imaging. *Magn Reson Med.* 2003; 50:955-965.
75. Liu T T, Frank L R. Efficiency, power, and entropy in event-related fMRI with multiple trial types. Part I: theory. *Neuroimage.* 2004; 21:387-400.
76. Tuch D S. Q-ball imaging. *Magn Reson Med.* 2004; 52:1358-1372.
77. Anderson A W. Measurement of fiber orientation distributions using high angular resolution diffusion imaging. *Magn Reson Med.* 2005; 54:1194-1206.
78. Descoteaux M, Angelino E, Fitzgibbons S, Deriche R. Apparent diffusion coefficients from high angular resolution diffusion imaging: estimation and applications. *Magn Reson Med.* 2006; 56:395-410.
79. Descoteaux M, Deriche R, Le Bihan D, Mangin J F, Poupon C. Multiple q-shell diffusion propagator imaging. *Med Image Anal.* 2011; 15:603-621.
80. Hosseinbor A P, Chung M K, Wu Y C, Alexander A L. Bessel Fourier Orientation Reconstruction (BFOR): an analytical diffusion propagator reconstruction for hybrid diffusion imaging and computation of q-space indices. *Neuroimage.* 2013; 64:650-670.
81 Özarslan E, Koay C G, Shepherd T M, Mean apparent propagator (MAP) MRI: a novel diffusion imaging method for mapping tissue microstructure. *NeuroImage.* 2013; 78:16-32.
82. Merlet S L, Deriche R. Continuous diffusion signal, EAP and ODF estimation via compressive sensing in diffusion M M. *Med Image Anal.* 2013; 17:556-572.
83. White N S, Leergaard T B, D'Arceuil H, Bjaalie J G, Dale A M. Probing tissue microstructure with restriction spectrum imaging: histological and theoretical validation. *Hum Brain Mapping.* 2013; 34:327-346.
84. Wedeen V J, Hagmann P, Tseng W Y, Reese T G, Weisskoff R M. Mapping complex tissue architecture with diffusion spectrum magnetic resonance imaging. *Magn Reson Med.* 2005; 54:1377-1386.
85. Özarslan E, Basser P. Microscopic anisotropy revealed by NMR double pulsed field gradient experiments with arbitrary timing parameters. *J Chem Phys.* 2008; 128: 154511.
86. Özarslan E, Shemesh N, Basser P. A general framework to quantify the effect of restricted diffusion on the NMR signal with applications to double pulsed field gradient NMR experiments. *J Chem Phys.* 2009; 130:104702.
87. Özarslan E. Compartment shape anisotropy (CSA) revealed by double pulsed field gradient M R. *J Magn Reson.* 2009; 199:56-67.
88. Shemesh N, Özarslan E, Basser P J, Cohen Y. Measuring small compartmental dimensions with low-q angular double-PGSE NMR: the effect of experimental parameters on signal decay. *J Magn Reson.* 2009; 198:15-23.
89. Shemesh N, Özarslan E, Bar-Shir A, Basser P J, Cohen Y. Observation of restricted diffusion in the presence of a free diffusion compartment: single- and double-PFG experiments. *J Magn Reson.* 2009; 200:214-225.
90. Shemesh N, Özarslan E, Komlosh M E, Basser P J, Cohen Y. From single-pulsed field gradient to double-pulsed field gradient M R: gleaning new microstructural information and developing new forms of contrast in M M. *NMR Biomed.* 2011; 23:757-780.
91. Paulsen J L, Özarslan E, Komlosh M E, Basser P J, Song Y Q. Detecting compartmental non-Gaussian diffusion with symmetrized double-PFG M M. *NMR Biomed.* 2015; 28:1550-1556.
92. Basser P J, Pierpaoli C. Microstructual and physiological features of tissues elucidated by quantitative diffusion tensor M M. *J Magn Reson B.* 1996; 111:209-219.
93. Armstrong R C, Mierzwa A J, Marion C M, Sullivan G M. White matter involvement after TBI: Clues to axon and myelin repair capacity. *Experimental Neurol.* 2016; 275:328-333

The invention claimed is:

1. A method for estimating local diffusion anisotropy and global tractography within neural architecture data, the method comprising:
   acquiring within a computer processor a first dataset and a second dataset from an imaging system configured to generate diffusion weighted magnetic resonance (dMRI) data for a target volume, the first dataset comprising single pulsed field gradient (sPFG) data and the second dataset comprising double pulsed field gradient (dPFG) data;
   using the computer processor, processing the first and second datasets separately or in parallel by:
      applying a spherical wave decomposition (SWD) algorithm to the first dataset to analyze morphological shape and segmentation for the target volume;
      applying a geometric optics-entropy spectrum pathways (GO-ESP) algorithm to the first dataset to identify ranked pathways between locations to detect macroscopic anisotropy and global tractography within the target volume;
      computing a weighted spin density function from the second dataset, wherein the weighted spin density function is 6-dimensional comprising a voxel coordinate and two 3-dimensional diffusion displacement coordinates on a radial grid defined within the target volume;
      defining a coupling matrix from the weighted spin density function to determine angular and radial variances within the second dataset, wherein the angular and radial variances are associated with diffusion properties for detecting microscopic anisotropy within the target volume;
   using the computer processor, integrating the detected macroscopic anisotropy and global tractography from the first dataset with the detected microscopic anisotropy from the second dataset using symplectomorphic registration (SYMREG) and joint estimation with space-time regularization (JESTER); and
   generating an output to a display device in communication with the computer processor, the output comprising an image corresponding to integrated macroscopic and microscopic anisotropy and global tractography within the target volume.

2. The method of claim 1, wherein the weighted spin density function is a function of a voxel coordinate and two 3-dimensional displacement coordinates within the second dataset.

3. The method of claim 1, wherein the weighted spin density function is constructed by determining angular standard deviation averaged over all radial dependencies to represent different angular variations of the spin density function and radial standard deviation averaged over all angular dependencies to represent different spatial scales of the weighted spin density.

4. The method of claim 3, further comprising generating a matrix of angular variances from the angular standard deviations and generating a matrix of radial variances from the radial standard deviations and mapping each matrix to a scalar quantity for visualization.

5. The method of claim 1, wherein the first dataset and the second dataset are acquired from the same dMRI pulse sequence.

6. A method for estimating local diffusion anisotropy and global tractography within neural architecture from diffusion weighted magnetic resonance image (dMRI) data, the method comprising using a computer processor to:
 integrate a first dataset comprising standard single pulsed field gradient (sPFG) dMRI data with a second dataset comprising double pulsed field gradient (dPFG) dMRI data, each dataset obtained for a target volume, into a common coordinate system with a same spatial resolution; and
 generate an output to a display device in communication with the computer processor, the output comprising an image corresponding to integrated macroscopic and microscopic anisotropy and global tractography within the target volume.

7. The method of claim 6, wherein, prior to integrating, the first dataset is processed by:
 applying morphological shape analysis and segmentation (SWD) for estimating simultaneous local diffusion and determining global tractography by determining entropy spectrum pathways combined with geometrical optics (GO-ESP) to estimate local voxel anisotropy and global connectivity.

8. The method of claim 6, wherein, prior to integrating, the second dataset is processed by computing a weighted spin density function, wherein the weighted spin density function is 6-dimensional comprising a voxel coordinate and two 3-dimensional diffusion displacement coordinates on a radial grid defined within the target volume.

9. The method of claim 6, wherein integrating comprises:
 using joint estimation in space-time regularization (JESTER) and symplectomorphic registration (SYMREG) to perform non-linear registration between modalities.

10. The method of claim 6, wherein the first dataset and the second dataset are acquired from the same dMRI pulse sequence.

11. A system for estimating local diffusion anisotropy and global tractography within neural architecture data, the system comprising:
 a memory storing computer-executable instructions;
 a processor in communication with the memory and configured to execute the computer-executable instructions to perform:
 acquiring a first dataset and a second dataset from an imaging system configured to generate diffusion weighted magnetic resonance (dMRT) data for a target volume, the first dataset comprising single pulsed field gradient (sPFG) data and the second dataset comprising double pulsed field gradient (dPFG) data;
 processing the first and second datasets separately or in parallel by:
  applying a spherical wave decomposition (SWD) algorithm to the first dataset to analyze morphological shape and segmentation for the target volume;
  applying a geometric optics-entropy spectrum pathways (GO-ESP) algorithm to the first dataset to identify ranked pathways between locations to detect macroscopic anisotropy and global tractography within the target volume;
  computing a weighted spin density function from the second dataset, wherein the weighted spin density function is 6-dimensional comprising a voxel coordinate and two 3-dimensional diffusion displacement coordinates on a radial grid defined within the target volume;
  defining a coupling matrix from the weighted spin density function to determine angular and radial variances within the second dataset, wherein the angular and radial variances are associated with diffusion properties for detecting microscopic anisotropy within the target volume;
 integrating the detected macroscopic anisotropy and global tractography from the first dataset with the detected microscopic anisotropy from the second dataset using symplectomorphic registration (SYMREG) and joint estimation with space-time regularization (JESTER); and
 generating an output to a display device in communication with the computer processor, the output comprising an image corresponding to integrated macroscopic and microscopic anisotropy and global tractography within the target volume.

12. The system of claim 11, wherein the weighted spin density function is a function of a voxel coordinate and two 3-dimensional displacement coordinates within the second dataset.

13. The system of claim 11, wherein the weighted spin density function is constructed by determining angular standard deviation averaged over all radial dependencies to represent different angular variations of the spin density function and radial standard deviation averaged over all angular dependencies to represent different spatial scales of the weighted spin density.

14. The system of claim 13, further comprising generating a matrix of angular variances from the angular standard deviations and generating a matrix of radial variances from the radial standard deviations and mapping each matrix to a scalar quantity for visualization.

15. The system of claim 11, wherein the first dataset and the second dataset are acquired from the same dMRI pulse sequence.

* * * * *